United States Patent
Dotan et al.

(10) Patent No.: US 7,537,900 B2
(45) Date of Patent: *May 26, 2009

(54) METHOD FOR DIAGNOSING MULTIPLE SCLEROSIS

(75) Inventors: Nir Dotan, Rehovot (IL); Avinoam Dukler, Modeiin (IL); Mikael Schwarz, Kiryat Uno (IL); Ari Gargir, Givatayim (IL)

(73) Assignee: Glycominds Ltd., Lod (IL)

( * ) Notice: Subject to any disclaimer, the term of this patent is extended or adjusted under 35 U.S.C. 154(b) by 436 days.

This patent is subject to a terminal disclaimer.

(21) Appl. No.: 10/634,309

(22) Filed: Aug. 4, 2003

(65) Prior Publication Data

US 2004/0077023 A1    Apr. 22, 2004

Related U.S. Application Data

(60) Provisional application No. 60/400,914, filed on Aug. 2, 2002, provisional application No. 60/447,076, filed on Feb. 13, 2003, provisional application No. 60/462,984, filed on Apr. 15, 2003, provisional application No. 60/473,231, filed on May 23, 2003.

(51) Int. Cl.
G01N 33/53    (2006.01)

(52) U.S. Cl. .................................. 435/7.1; 436/811

(58) Field of Classification Search .................. None
See application file for complete search history.

(56) References Cited

U.S. PATENT DOCUMENTS 6,972,172 B2    12/2005    Dukler et al. .................. 435/6

FOREIGN PATENT DOCUMENTS

| WO | WO 00/49412 | | 8/2000 |
|---|---|---|---|
| WO | WO 02/18950 | A1 | 3/2002 |
| WO | WO 03/000733 | A2 | 1/2003 |

OTHER PUBLICATIONS

Schwarz, M., et al. J. Neuro. Sci. 2006;244:59-68.*
Mazzucco, S., et al. Bioorg. Med. Che, lett. 1999;9:167-172.*
Bozzaro, et al., "Monoclonal Antibodies against Dictyostelium Plasma Membranes: their Binding to Simple Sugars", *Cell Differentiation*, 17:83-94 (1985).
Matsuda, et al., "Antibody Response to Haptenic Sugar Antigen: Immunodominancy of Protein-Bound Lactose Formed by Amino-Carbonyl Reaction", *Mol. Immun.*, 24(5):421-425 (1987).
Papini, et al., "[Asn$^{31}$(N-β-D-Glucopyranosyl)] hMOG(30-50): An Antigen to Identify Anti-hMOG Peptide Antibodies in Multiple Sclerosis Patients", *Proceedings of the 10$^{th}$ International Congress of Immunology*, Monduzzi Editore, pp. 1239-1244 (1998).
Berger, et al., "Antimyelin Antibodies as a Predictor of Clinically Definite Multiple Sclerosis after a First Demyelinating Event", *N. Engl. J. Med.*, 349:139-145 (2003).
Saveliev, et al., "Amylolytic Activity of IgM and IgG Antibodies from Patients with Multiple Sclerosis", *Immun. Letters*, 86:291-297 (2003).
Carotenuto, et al., "Conformational Analysis of a Glycosylated Human Myelin Oligodendrocyte Glycoprotein Peptide Epitope Able To Detect Antibody Response in Multiple Sclerosis", *J. Med. Chem.*, 44:2378-2381 (2001).
Bao *J. Chromatogr. B.*, 699(1+2):463-480 (1997).
Brex et al. *N. Engl. J. Med.*, 346(3):158-164 (2002).
Comi et al. *Lancet*, 357:1576-1582 (2001).
Holme et al. *Carbohydr. Res.*, 8:43-55 (1968).
Hou et al. *J. Immunol.*, 170:4373-4379 (2003).
Jacobs et al. *Ann. Neurol.*, 41(3):392-398 (1997).
Jacobs et al. *N. Engl. J. Med.*, 343(13):898-904 (2000).
Kurtzke *Neurol.*, 33(11):1444-1452 (1983).
McDonald et al. *Ann. Neurol.*, 50(1):121-127 (2001).
O'Riordan et al. *Brain*, 121:495-503 (1998).
Poser et al. *Ann. Neurol.*, 13(3):227-231 (1983).
Rongen et al. *J. Immunol. Meth.*, 204(2):105-133 (1997).
Schmalzing et al. *Electrophoresis*, 18(12-13):2184-2193 (1997).
Schwarz et al. *Glycobiol.*, 13(11):749-754 (2003).
Self et al. *Curr. Opin. Biotechnol.*, 7:60-65 (1996).
Weinshenker et al. *Brain*, 112(part VI):1419-1428 (1989).
Zhan et al. *Biochem. Biophys. Res. Commun.*, 308(1):12-22 (2003).

* cited by examiner

*Primary Examiner*—G. R Ewoldt
(74) *Attorney, Agent, or Firm*—Mintz, Levin, Cohn, Ferris, Glovsky and Popeo, PC; Ingrid A. Beattie

(57) ABSTRACT

Disclosed is a method for diagnosing multiple sclerosis and more particularly to a method for diagnosing multiple sclerosis by measuring levels of antibodies to glycans in a biological sample.

7 Claims, 24 Drawing Sheets

METHOD FOR DIAGNOSING MULTIPLE SCLEROSIS

RELATED APPLICATIONS

This application claims priority to U.S. Ser. No. 60/400,914, filed Aug. 2, 2002; U.S. Ser. No. 60/447,076, filed Feb. 13, 2003; U.S. Ser. No. 60/462,984 filed Apr. 15, 2003; and U.S. Ser. No. 60/473,231, filed May 23, 2003. The contents of these applications are incorporated herein by reference in their entireties.

FIELD OF THE INVENTION

The invention relates generally to a method for diagnosing multiple sclerosis and more particularly to a method for diagnosing multiple sclerosis by measuring levels of antibodies to glycans in a biological sample.

BACKGROUND OF THE INVENTION

Multiple sclerosis (MS) is a chronic autoimmune inflammatory disease of the central nervous system. It is a common cause of persistent disability in young adults. In patients suffering from MS, the immune system destroys the myelin sheet of axons in the brain and the spinal chord, causing a variety of neurological pathologies. In the most common form of MS, Relapsing-Remitting, episodes of acute worsening of neurological function (exacerbations, attacks) are followed by partial or complete recovery periods (remissions) that are free of disease progression (stable). It has been reported that ninety percent of patients with MS initially present with a clinically isolated syndrome because of an inflammatory demyelinating lesion in the optic nerve, brain stem, or spinal cord. About thirty percent of those patients with a clinically isolated syndrome progress to clinically definite MS within 12 months after presentation. The subsequent progression of the disease can vary significantly from patient to patient. The progression can range from a benign course to a classic relapsing-remitting, chronic progressive, or rare fulminant course.

A method for diagnosing MS that facilitates early detection of clinically definite MS would be valuable for both managing the disease and providing counsel for the patient. For example, patients diagnosed early with clinically definite MS could be offered disease modifying treatments that have recently been shown to be beneficial in early MS.

Current methods for assessment and tracking progress of MS are based on assessment and scoring of patients' function in attacks and accumulated disabilities during the attacks. One assessment used to assess MS is the commonly used Expanded Disability Status Scale (EDSS). However, EDSS is based on a subjective assessment of patient function.

Methods for diagnosis can also include tracking brain lesions by Magnetic Resonance Imaging (MRI) or testing Cerebrospinal Fluid (CSF) for Oligo-Clonal Banding (OCB). MRI is a physical method for assessment of brain lesions and is expensive for routine use. Moreover, the correlation between MRI results and disease activity is poor. Cerebrospinal Puncture is an un pleasant invasive procedure that is not suitable for routine use. In addition, both methods assess damage only after it has occurred; neither method can predict the onset of attacks. A further disadvantage in testing for OCB in CSF and MRI as a way to diagnose MS is that a negative OCB or MRI will not preclude the existence of MS.

There is a need for a method that uses objectively assessed markers for diagnosing MS and for predicting the onset of attacks in patients suffering from MS.

SUMMARY OF THE INVENTION

The invention is based in part on the discovery that MS patients have elevated serum levels of auto antibodies of IgG, IgA, IgM that bind the glycan structures Glc ($\alpha$) or Glc ($\alpha$ 1-4) Glc ($\alpha$) or Glc ($\alpha$ 1-4) Glc ($\beta$) as compared to the serum levels of these autoantibodies in healthy individuals. In addition, the same autoantibodies specific for these glycan structures are elevated during the exacerbation state as compared to the level observed in patients in remission and healthy individuals. A high correlation has also been observed between IgM anti-Glc ($\alpha$)antibody serum levels in females, clinically diagnosed (relapsing-remitting) MS patients, and the women's EDSS (Expanded Disability Status Scale) score. The high correlation indicates that the levels of IgM anti-$\alpha$-Glucose in serum can act as a clinical surrogate endpoint marker for the activity of the disease and a way to track the efficacy of a drug compound in clinical trials.

Monitoring the levels of those antibodies in the blood of MS suspected patients facilitates quick and cost effective early diagnosis of MS patients and early prescribing of disease modifying drugs. Monitoring of the levels of those antibodies in the blood of defined MS patients will also enable quick and cost effective monitoring of the effects of prescribed drugs, and early detection of attacks, enabling early prophylactic treatment.

Among the additional advantages of the invention are that the existence of MS in patients can be determined at an earlier stage of the disease, when its symptoms may resemble many other MS-like diseases. Early diagnosis allows physicians to treat MS earlier in the course of the disease, thereby minimizing or preventing the damage caused by the destruction of myelin and disabilities brought about by this destruction. In addition, the methods disclosed herein enable physicians to follow MS patients regularly in order to assess the disease severity, to monitor therapy, and change treatment once signs for coming attacks appear. For example, an increase in biomarkers indicative of an MS attack may warrant administration to the patient of methylpredisone, which is a general anti inflammatory agent commonly administered during attacks.

The methods disclosed herein can also be used to select the best drug treatment for a specific patient. For example, a patient may start the treatment course with a certain drug, and the change in the marker levels will be indicative for the effectiveness of drug. Reversion of marker levels to a diseased state indicates the drug is losing effectiveness, and the drug can be replaced with a second drug after a short time period. Otherwise, a physician will have to wait for the next attacks to determine if the drug is effective for the specific patient.

The biomarkers disclosed herein can additionally act as a surrogate end point for assessing the response of a patient to the tested drug in a cost effective way. A surrogate end point based on a serological test facilitates efficient testing of new potential MS drugs.

In one aspect, the invention features a method of diagnosing multiple sclerosis in a subject. The method includes providing a test sample from a subject and detecting in the test sample at least one biomarker that is an antibody that binds specifically to a glycan structure. The antibody can be, e.g., an anti-Glc ($\alpha$) antibody, an anti-Glc ($\alpha$ 1-4) Glc ($\alpha$) antibody, an anti-Glc ($\alpha$ 1-4) Glc ($\beta$) antibody, an anti-Glc ($\beta$) antibody, an anti-Gal ($\beta$) antibody; an anti-Glc ($\beta$ 1-4) Glc ($\beta$ 1-4) Glc ($\beta$)antibody, an anti-GlcNAc ($\beta$ 1-4) GlcNAc ($\beta$)antibody, an anti-L-Araf ($\alpha$)antibody, an anti-L-Rha ($\alpha$)antibody, an anti-Gal ($\beta$1-3) [GlcNAc ($\beta$1-6)] GalNAc ($\alpha$)antibody, an anti-Gal ($\beta$ 1-4) GlcNAc ($\alpha$)antibody, an anti-Gal ($\beta$ 1-3) GalNAc ($\alpha$), an anti-Gal ($\beta$ 1-3) GlcNAc ($\beta$), an anti-GlcA ($\beta$) antibody, or an anti-GlcA (β) antibody, or an anti-Xyl (α) antibody. The levels of antibody or antibodies in the test sample are compared to a control sample, which is derived from one or more individuals who show multiple sclerosis symptoms and whose that have multiple sclerosis symptoms with a known multiple sclerosis status, or from an individual or individuals who do not show multiple sclerosis symptoms. MS status can include, e.g., exacerbations, attacks, remissions, and stable stages of the disease.

In various embodiments, at least 2, 3, 4, 5, 6, 7, 8, 9, 10, 11, 12, 13, 14, 15, 16, 17 or 18 of these antibodies are detected. In some embodiments, the antibody detected in the test sample is an anti-Glc (α)antibody, an anti-Glc (α 1-4) Glc (α) antibody or both an anti-Glc (α) antibody and an anti-Glc (α 1-4) Glc (α) antibody.

In some embodiments, the control sample consists essentially of a population of one or more individuals that do not show symptoms of a multiple sclerosis. In other embodiments, the control sample consists essentially of a population who do show symptoms of a multiple sclerosis. The presence of MS in the control sample can be determined using techniques known in the art, e.g., an Expanded Disability Status Scale (EDSS) assessment or a Magnetic Resonance Imaging (MRI) assessment, or both.

The test sample can be, e.g., a biological fluid. Examples of biological fluids include, e.g., whole blood, serum, plasma, spinal cord fluid, urine, or saliva.

The subject can be either a female or a male.

The antibody detected can be, e.g., an IgM type or an IgA type or an IgG antibody.

In some embodiments, the type of multiple sclerosis detected is early multiple sclerosis.

Also provided by the invention is a method of diagnosing a multiple sclerosis exacerbation in a subject. The method includes providing a test sample from a subject and detecting an anti-Glc (α)IgM type antibody and/or an anti-Glc (α 1-4) Glc (α) IgM type antibody in the test sample. The levels of the antibody in the test sample are compared to a control sample, which is derived from one or more individuals whose multiple sclerosis status is known.

In some embodiments, the control sample consists essentially of a population of one or more individuals that do not show symptoms of a multiple sclerosis exacerbation and whose multiple sclerosis status is in remission. A multiple sclerosis exacerbation is diagnosed in the subject if more anti Glc (α)antibody or anti-Glc (α 1-4) Glc (α)antibody is present in the test sample than in the control sample. In other embodiments, the control sample consists essentially of a population of one or more individuals that show symptoms of a multiple sclerosis exacerbation, and a multiple sclerosis exacerbation is diagnosed in the subject if levels of anti-Glc (α)IgM type antibody and/or anti-Glc (α 1-4) Glc (α)IgM type antibody are present in similar amounts in the test sample and the control sample.

The test sample can be, e.g., a biological fluid. Examples of biological fluids include, e.g., whole blood, serum, plasma, spinal cord fluid, urine, or saliva.

The subject can be either a female or a male.

The antibody detected can be, e.g., an IgM type or an IgA or an IgG type antibody.

In some embodiments, the diagnosis is an early diagnosis of multiple sclerosis exacerbation.

In some embodiments, the subject has been treated with an MS therapeutic agent, e.g., interferon beta or glitamerer acetate administered subcutaneously.

Also within the invention is method for assessing multiple sclerosis disease severity in a subject. The method includes providing a test sample from a subject and determining whether the test sample contains an anti-Glc (α)IgM type antibody and/or an anti Glc (α 1-4) Glc (α)IgM type antibody. The amount of antibody in the test sample is compared to the amount of the antibody in the control sample, which is derived from one or more individuals whose multiple sclerosis disease severity is known.

In some embodiments, the control sample consists essentially of a population of one or more individuals whose multiple sclerosis disease severity is defined by Expanded Disability Status Scale (EDSS), changes in an EDSS score, or a Magnetic Resonance Imaging (MRI) assessment.

The test sample can be, e.g., a biological fluid. Examples of biological fluids include, e.g., whole blood, serum, plasma, spinal cord fluid, urine, or saliva.

If desired, the method may further include selecting a therapeutic agent for treating multiple sclerosis by selecting a therapeutic agent and dosage regimen based on the relative levels of the antibody or antibodies in the test sample and the control sample.

In some embodiments, higher levels of antibodies in the test sample relative to the control sample indicate selection of a therapeutic agent and dosage regimen that is subcutaneous administration of interferon beta(BETAFERON®, AVONEX®, REBIF®) or subcutaneous administration of glitamerer acetate (COPAXONE®).

The subject can be either a female or a male.

Also provided by the invention is a kit for diagnosing symptoms associated with multiple sclerosis. The kit include a first reagent that specifically detects an anti-Glc (α)antibody, a second reagent that specifically detects an anti-Glc (α 1-4) Glc (α)antibody, and directions for using the kit. The kit optionally includes a reagent that specifically detects an IgM type antibody.

Also within the invention are substrates that include reagents that specifically detect the antibodies disclosed herein, e.g., an anti-Glc (α) antibody, an anti-Glc (α 1-4) Glc (α) antibody, an anti-Glc (α 1-4) Glc (β) antibody, an anti-Glc (β) antibody, an anti-Gal (β) antibody; an anti-Glc (β 1-4) Glc (β 1-4) Glc (β)antibody, an anti-GlcNAc (β 1-4) GlcNAc (β)antibody, an anti-L-Araf (α)antibody, an anti-L-Rha (α)antibody, an anti-Gal (β1-3) [GlcNAc (β1-6)] GalNAc (α)antibody, an anti-Gal (β 1-4) GlcNAc (α)antibody, an anti-Gal (β 1-3) GalNAc (α), an anti-Gal (β 1-3) GlcNAc (β), an anti-GlcA (β) antibody, or an anti-GlcA (β) antibody, or an anti-Xyl (α) antibody. The substrate can be, e.g., planar.

In a further aspect, the invention provides a method of selecting a therapeutic agent for treating multiple sclerosis. The method includes providing a test sample from a subject diagnosed with, or at risk for, multiple sclerosis and determining whether the test sample contains an anti-Glc (α) antibody. Levels of the antibody in the test sample to are compared to levels of antibody in a control sample consisting essentially of one or more individuals whose multiple sclerosis disease severity is known. A therapeutic agent and dosage regimen is selected based on the relative levels of the antibody in the subject sample and the control sample.

In some embodiments, the method further includes determining whether the test sample contains an anti-Glc (α 1-4) Glc (α)antibody and comparing the levels of the anti-Glc (α 1-4) Glc (α)antibody in the test sample to levels of antibody in a control sample consisting essentially of one or more individuals whose multiple sclerosis disease severity is known In some embodiments, the control sample consists essentially of one or more individuals whose status is no multiple sclerosis or stable multiple sclerosis.

Unless otherwise defined, all technical and scientific terms used herein have the same meaning as commonly understood by a person of ordinary skill in the art to which this invention belongs. Although methods and materials similar or equivalent to those described herein can be used in the practice or testing of the present invention, suitable methods and materials are described below. All publications, patent applications, patent, and other references mentioned herein are incorporated by reference in their entirety. In the case of conflict, the present specification, including definitions, will control. In addition, the materials, methods, and examples are illustrative only and not intended to be limiting.

Other features and advantages of the invention will be apparent from the following detailed description and claims.

BRIEF DESCRIPTION OF THE DRAWINGS

FIG. 10A shows an p-amino phenyl P-saccharide covalently linked at its reducing end to a solid surface via a linker.

FIG. 10B shows batch-to-batch reproducibility of binding of biotinylated WGA to the glycan array. Three separate batches of arrays were assayed simultaneously with biotinylated WGA FIG. 10C shows a competition assay with ConA to bound Man ($\alpha$). Increasing concentrations of soluble Mannose or Gal ($\beta$ 1-4) Glc were incubated with biotinylated ConA (1.5 µg/ml) for 1 hr, and detected with Streptavidin conjugated to Europium.

FIG. 10D shows the specificity of lectin binding to different anomers. ConA binding to negative control Glycerol (19), Man ($\alpha$) (26) and Man ($\beta$) (27). GSI binding to -Gal ($\alpha$) (1), Gal ($\beta$) (2), GalNAc ($\alpha$) (7), and GalNac ($\beta$) (8).

FIG. 10E shows plate-to-plate reproducibility of the glycan array. Five identical plates presenting GlcNac ($\beta$) were probed with biotinylated WGA.

DETAILED DESCRIPTION OF THE INVENTION

Figure 1:
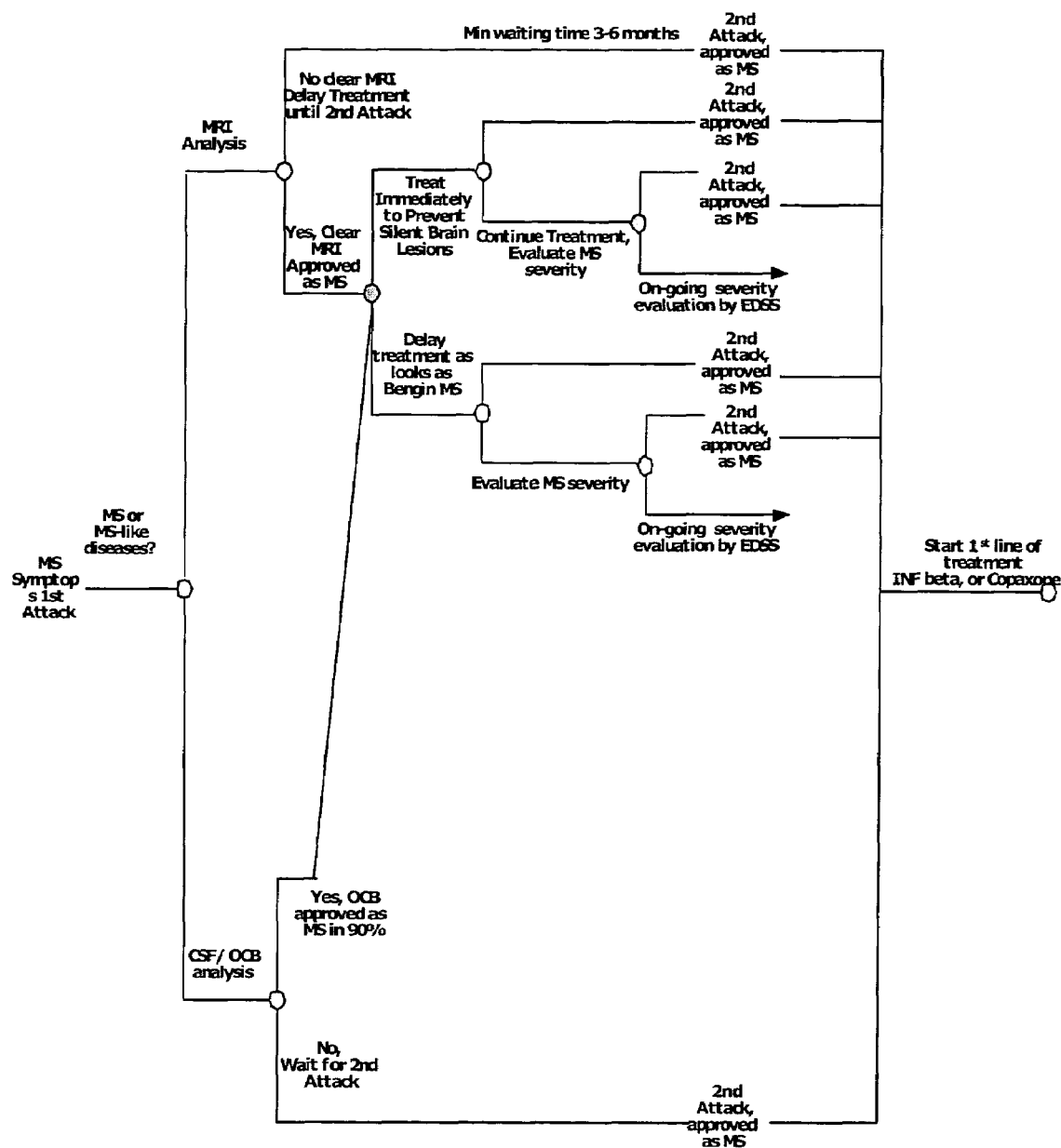
FIG. 1 shows the decision tree for determining that a MS suspected patient actually has MS.

The methods provided herein allow for early diagnosis of initial and recurring multiple sclerosis using objectively assessed biomarker levels. The current decision tree for diagnosing a patient with MS is described in FIG. 1. A patient with acute worsening of neurological function initially has to be diagnosed as a defined MS patient before being eligible for treatment with disease modifying drugs. The physician will have to determine if the patient has MS like symptoms (such as Younger stroke, Lupus, Vitamin B-12 deficiency, Anti phospholipid syndrome, Severe Migraine) or if they actually have MS. The patient will have to experience a second acute worsening of neurological function (attack) before being diagnosed as a MS patient and be able to start chronic treatment with a MS therapeutic agent such as interferon beta or glatiramer acetate.

Currently, physicians are using MRI for the identification of the existence of brain lesions and/or the testing of Cerebrospinal Fluid (CSF) for Oligo Clonal Banding (OCB). If MRI gives a clear result regarding the existence of brain lesions or the presence of OCB in the CSF, the physician may start treatment immediately in order to prevent silent brain lesions. A diagnosis of full MS diagnosis is currently made only after the second attack. In case MRI does not give a clear result or there are no OCB in the patients CSF, no MS is diagnosed and treatment is delayed until following a second attack.

The method disclosed herein can be performed by extracting blood from a patient with acute worsening of neurological function and suspected to have MS. The method can identify the existence of MS by measuring anti-Glc ($\alpha$) and anti-Glc ($\alpha$ 1-4) Glc ($\alpha$) IgM level. If the level of at least one of these antibodies is significantly higher then the average level of these antibodies in sera of healthy individuals, the patient is diagnosed as an MS patient without the need to wait for a second attack. In addition, the quick diagnosis allows for treatment to begin immediately.

Figure 2:
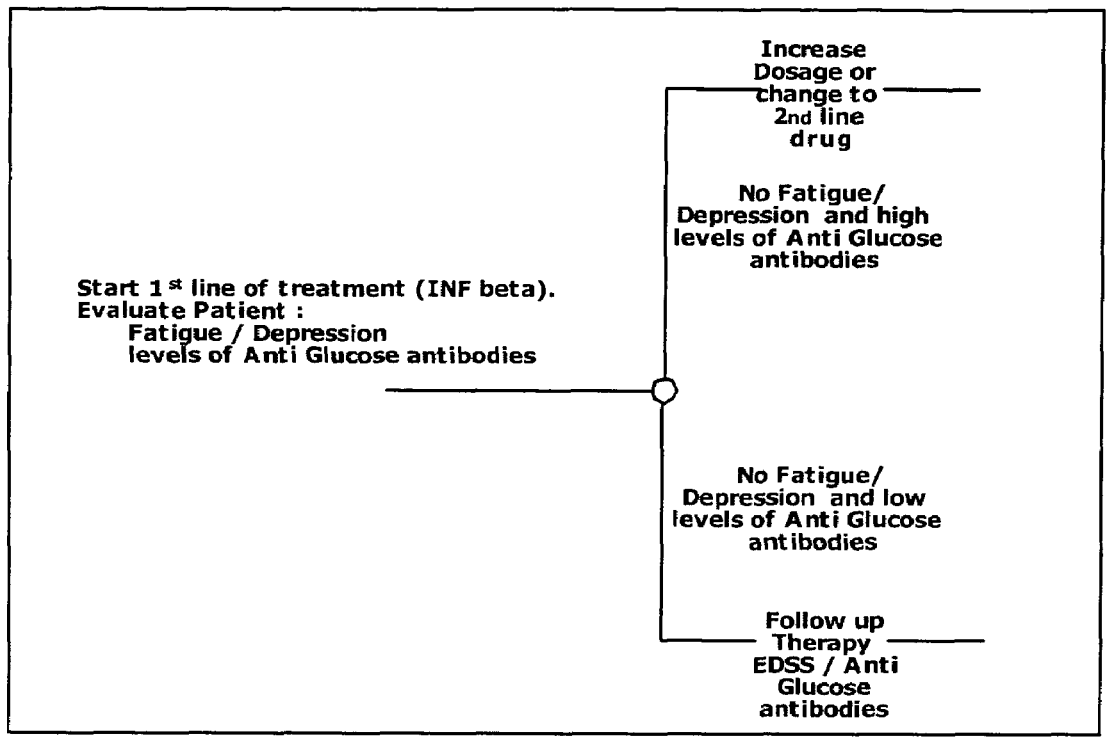
FIG. 2 shows the decision tree for selecting a drug and dose for an MS patient based on levels of anti Glc ($\alpha$ 1-4) Glc ($\alpha$) or Glc ($\alpha$) antibodies.
Figure 2:
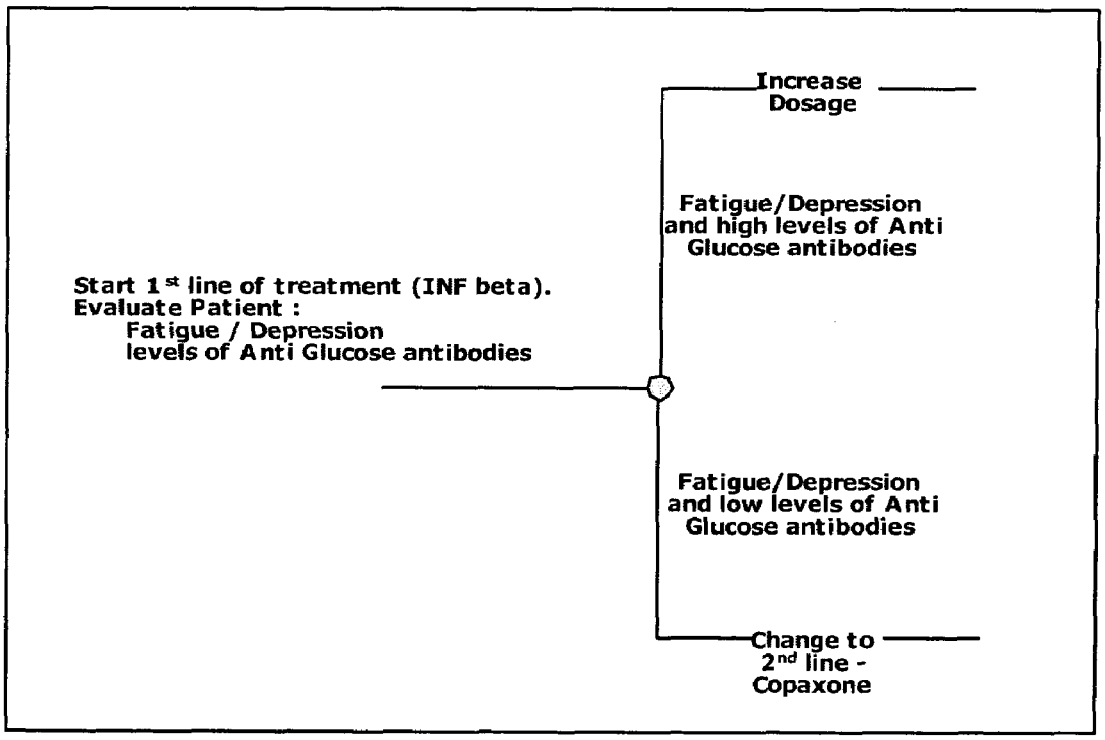

One first line of treatment for MS is interferon $\beta$ (e.g., INF$\beta$-1a and INF$\beta$-1b). The current evaluation of effectiveness and required dosage of the drug is based on continued monitoring of several clinical scores. Currently, the EDSS score and its change over time (e.g., by comparing the difference in the EDSS every 3-6 months) is the main clinical parameter for disease management. An important component of the assessment is the level of fatigue and depression experienced by the patient. The fatigue and or depression can be a symptom of MS, as an autoimmune disease, or a side effect from the usage of interferon beta. Identifying the cause of the fatigue is important for managing the treatment. For example, if the fatigue is a result of a side effect of the interferon, the physician will consider lowering the dosage or even exchanging it for another drug. However, if the fatigue is due to the MS symptoms, the physician will have to consider increasing the drug dosage (see FIG. 2).

Screening the patient's blood and determining the level of biomarkers disclosed herein, e.g., the IgM antibodies anti Glc ($\alpha$) and anti Glc ($\alpha$ 1-4) Glc ($\alpha$) herein allows for accurate monitoring of therapy. Significantly decreases in antibody levels indicates that the patient is responding well to the given drug.

Early Detection of Attacks

Figure 3:
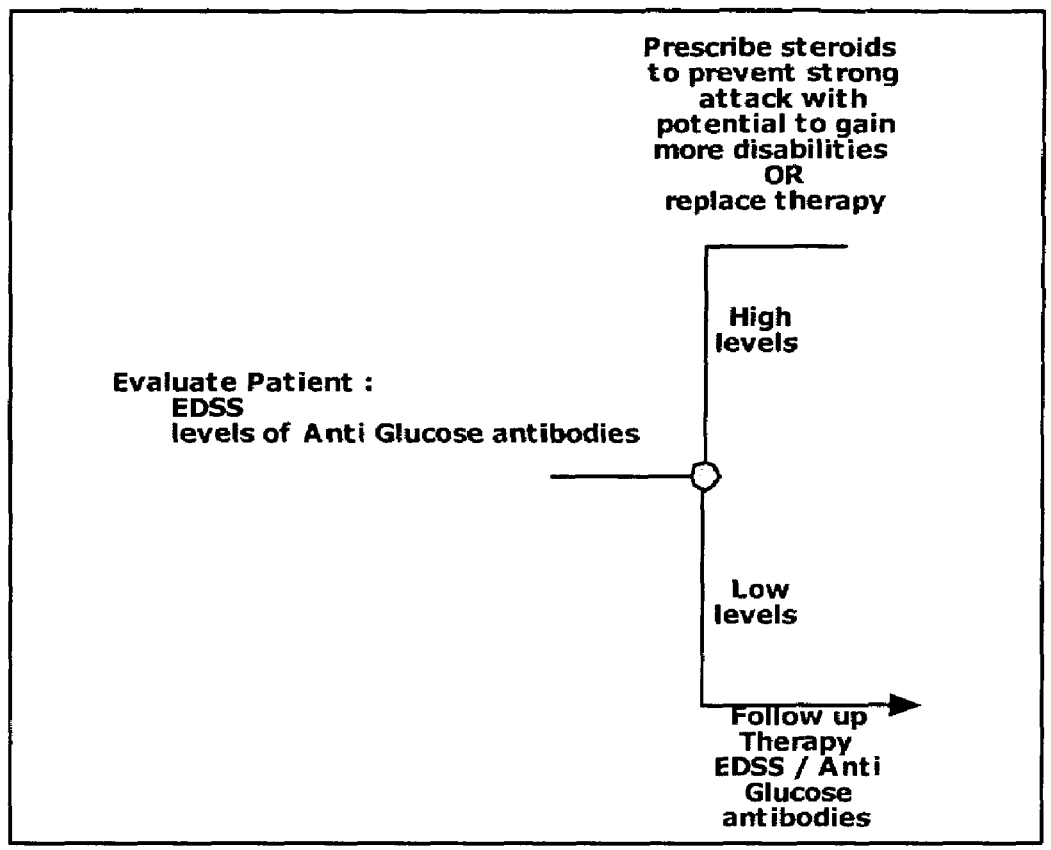
FIG. 3 shows the decision tree for prediction and early diagnosis of attacks in MS patients.
Figure 7:
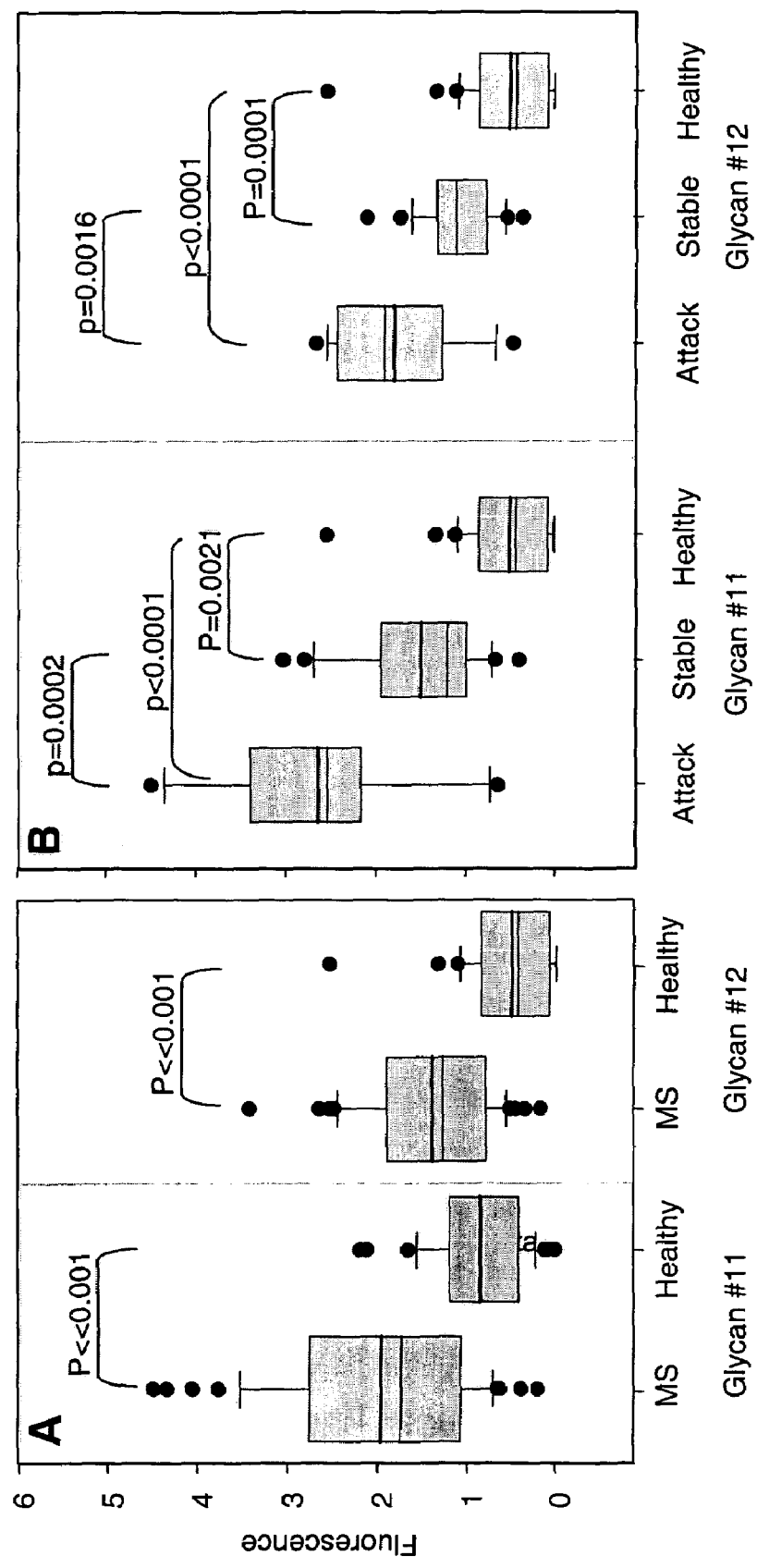
FIG. 7A is a graph showing the average signal from binding of anti Glc ($\alpha$), (Glycan #11) and Glc ($\alpha$ 1-4) Glc ($\alpha$), (Glycan #12)IgM in MS and healthy populations.
FIG. 7B is a graph showing the average signal from binding of anti Glc ($\alpha$) Glycan #11 and Glc ($\alpha$ 1-4) Glc ($\alpha$) Glycan #12IgM in MS patients in attack, stable MS patients and healthy populations.

Currently there is no way to predict the onset of attacks in MS patients. MRI and clinical evaluation of the patients can only reveal damage that has already occurred. Periodical measurement of the level of a few anti glycan antibodies (for example anti-Glc ($\alpha$) IgM or anti-Glc ($\alpha$ 1-4) Glc ($\alpha$) IgM) in the patient's blood according to the method described herein allows for physicians to identify upcoming attacks based upon an increase in levels of these antibodies. Levels of these antibodies are significantly higher in the blood of patients in MS attack situations vs. patients in a stable state (see FIG. 7). Upon detection of an increase in those antibodies, the physician can start an aggressive steroid treatment to reduce the inflammation and prevent damage to the myelin (see FIG. 3).

Also provided herein are methods of identifying and assessing individuals with atherosclerosis at risk for stable and unstable angina using antibody biomarkers specific for glycans, as well the use of immobilized glycans to detect cells of interest.

Various glycans structures are discussed in this application. The glycans are presented either in the International Union of Pure and Applied Chemistry (IUPAC) condensed form for nomenclature carbohydrate representation or in LINEARCODE® syntax, for linearcode syntax principals see (Banin E. Neuberger Y. Altshuler Y. Halevi A. Inbar O. Dotan N. and Dukler A. (2002) A Noval Liner Code Nomenclature for complex Carbohydrates. Trends in Glycoscience and Glycotechnology Vol. 14 No. 77 pp. 127-137). Translation of LINEARCODE to IUPAC representation is in Table 1.

Figure 10:
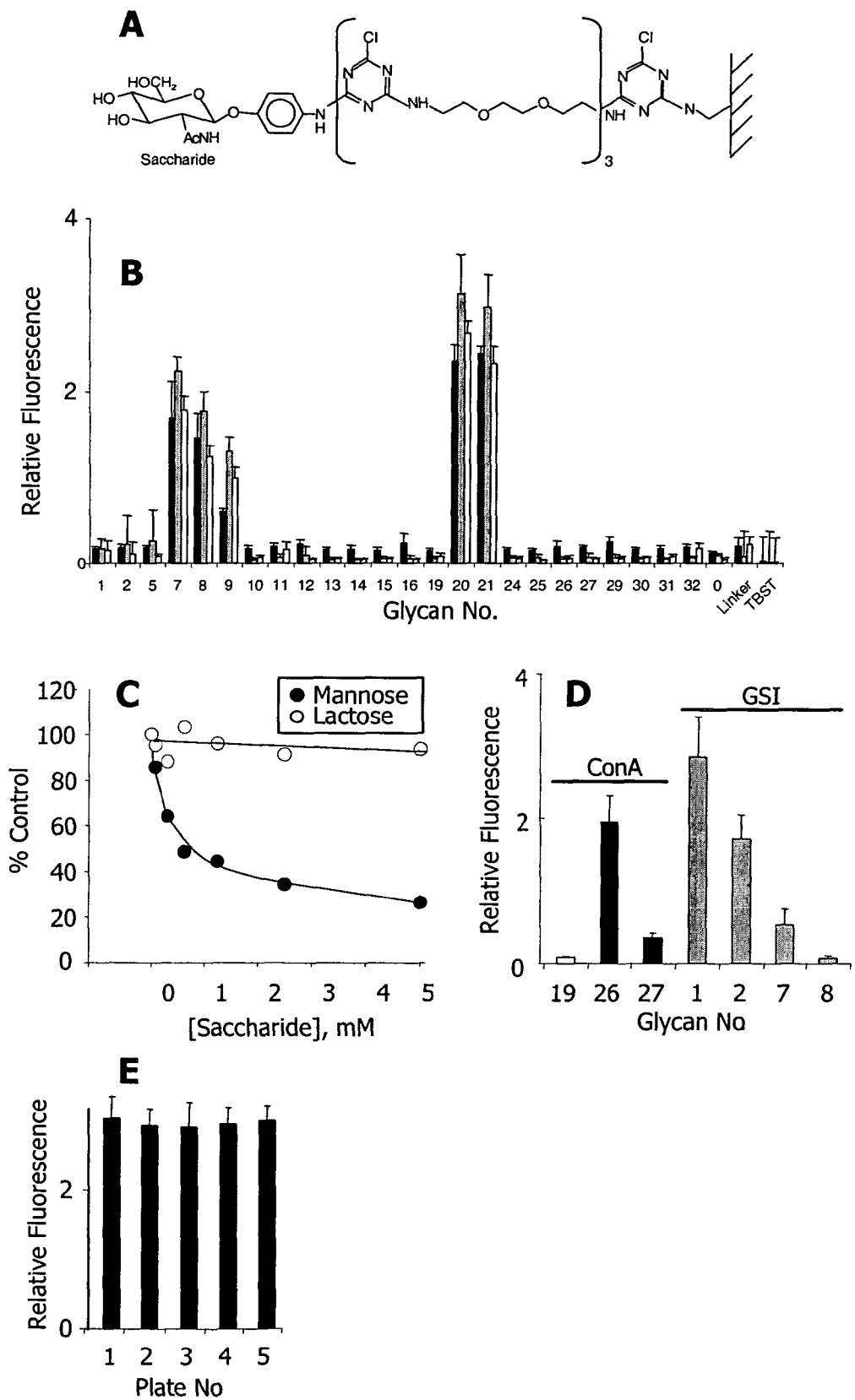
FIGS. 10A-10E show the glycan array; chemical structure, specificity of Lectin interaction and reproducibility.

All the glycan structures that discussed in this disclosere, unless mentioned otherwise are connected to in the indicated anomericity α or β through linker to solid phase as described in FIG. 10 A.

The invention will be illustrated in the following non-limiting examples.

EXAMPLE 1

Comparison Between Antiglycan Antibodies in the Serum of Multiple Sclerosis (MS) Patients and Normal Population An anti-glycan antibody (Igs) profile was obtained using GlycoChip® arrays (Glycominds, Ltd., Lod, Israel, Cat No. 9100). The arrays were constructed using procedures described in WO00/49412. Anti-glycan antibody profiles of 40 multiple sclerosis patients and 40 sex and aged matched normal blood donors were compared.

All serum samples were tested using GlycoChip® plates (Glycominds Ltd., Lod, Israel, Cat No. 9100), which was an array of mono and oligosaccharide covalently attached to a reduced volume 384 wells micro titer plate. The mono and oligosaccharides displayed on the array are listed in FIG. 4. A translation of the LinearCode™ syntax used to describe glycan structure to IUPAC nomenclature can be found in Table 1.

The sera of healthy volunteers and MS patients volunteers who had signed an informed consent form were collected in evacuated silicon coated gel containing tubes (Estar Technologies Cat#616603GLV). The sera were separated from the blood cells and kept frozen in −25° C. until use. They were analyzed in two separate experiments, each repeated twice on separate days.

Sera from volunteers were diluted (1:20) in TBST dispensed into a GlycoChip® plate using a Tecan Genesis Workstation 200 robot (10 μL/well) and incubated 30 min at 25° C. There were 4 repeats for each glycan and serum sample on the plate.

The plates were washed with 250 μL/well of high salt buffer (0.15M KNa pH 7.2, NaCl 2M, $MgSO_4$ 0.085M, 0.05% Tween20) in an automatic plate washer (Tecan, PowerWasher™). Ten μl/well of biotinylated protein A (ICN 62-265), 1 μg/ml in TBST, was dispensed manually and the plates incubated for 30 min at 25° C. The plate was washed again with high salt buffer.

Streptavidin-conjugated Europium, Wallac, AD0062 (1μ/ml, 10 μl/well) was added manually followed by incubation for 30 min at 25° C. in the dark. Washing of the plates with the high salt buffer was repeated. Delfia™ enhancement buffer, (Wallac, 730232, 10 μl/well) was added to the wells and the plates were incubated at least 30 min in the dark. The fluorescence of the wells was read with Victor 1420 (Wallac) using time resolved fluorescence settings Emi. 612 nm and Ext. 340 nm.

Figure 4:
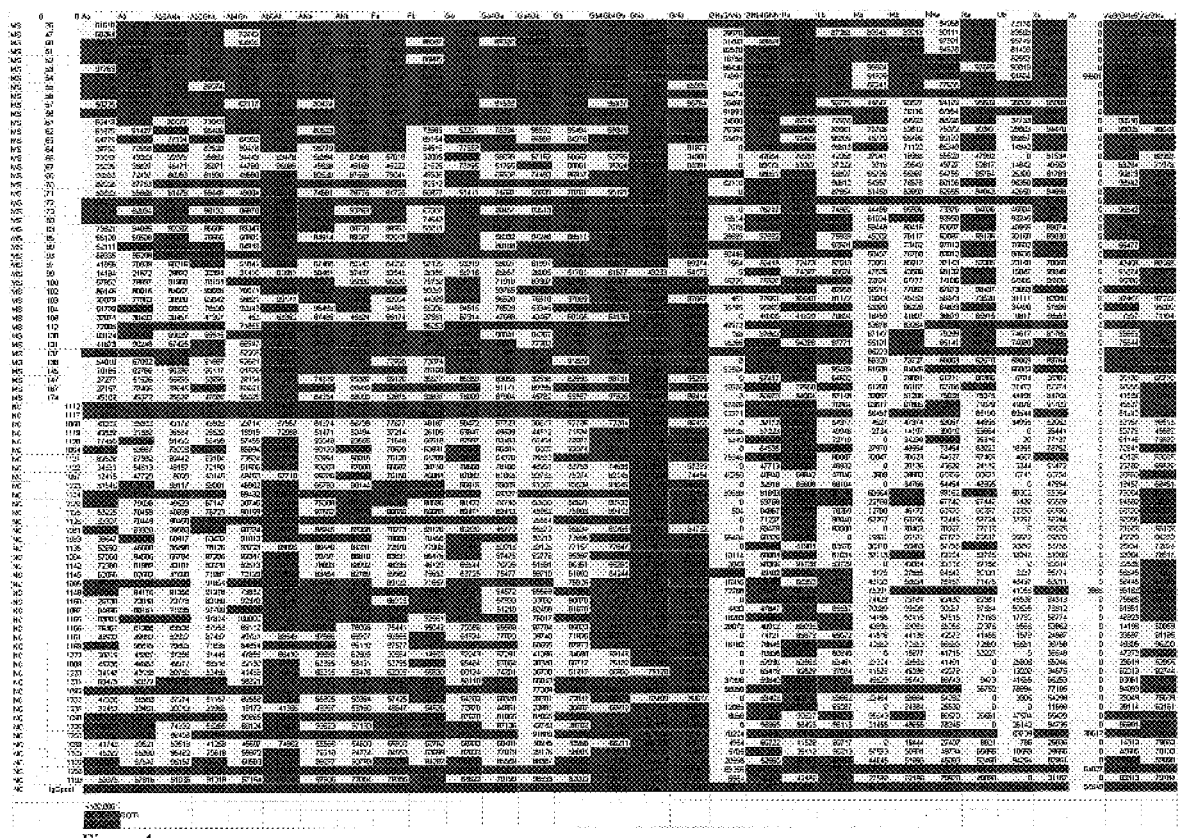
FIG. 4 is a table showing the relative fluorescence from binding of different anti glycan antibodies in MS patients as well as in normal individuals. The glycans structures are presented in the upper line of the table in LINEARCODE® syntax.

The profiles of all the tested patients are displayed in FIG. 4. The upper 40 lines (MS) describe the anti-carbohydrate level of MS samples, and the lower 40 lines (NC) describe the anti-carbohydrate level of samples from normal control population. The values presented are absolute values without background reduction. Since the detection of bound antibodies was done with biotinylated protein A, which binds to IgG, IgA and IgM., the signal represents the total binding of antibodies from all sub types IgG, IgA and IgM.

Figure 5:
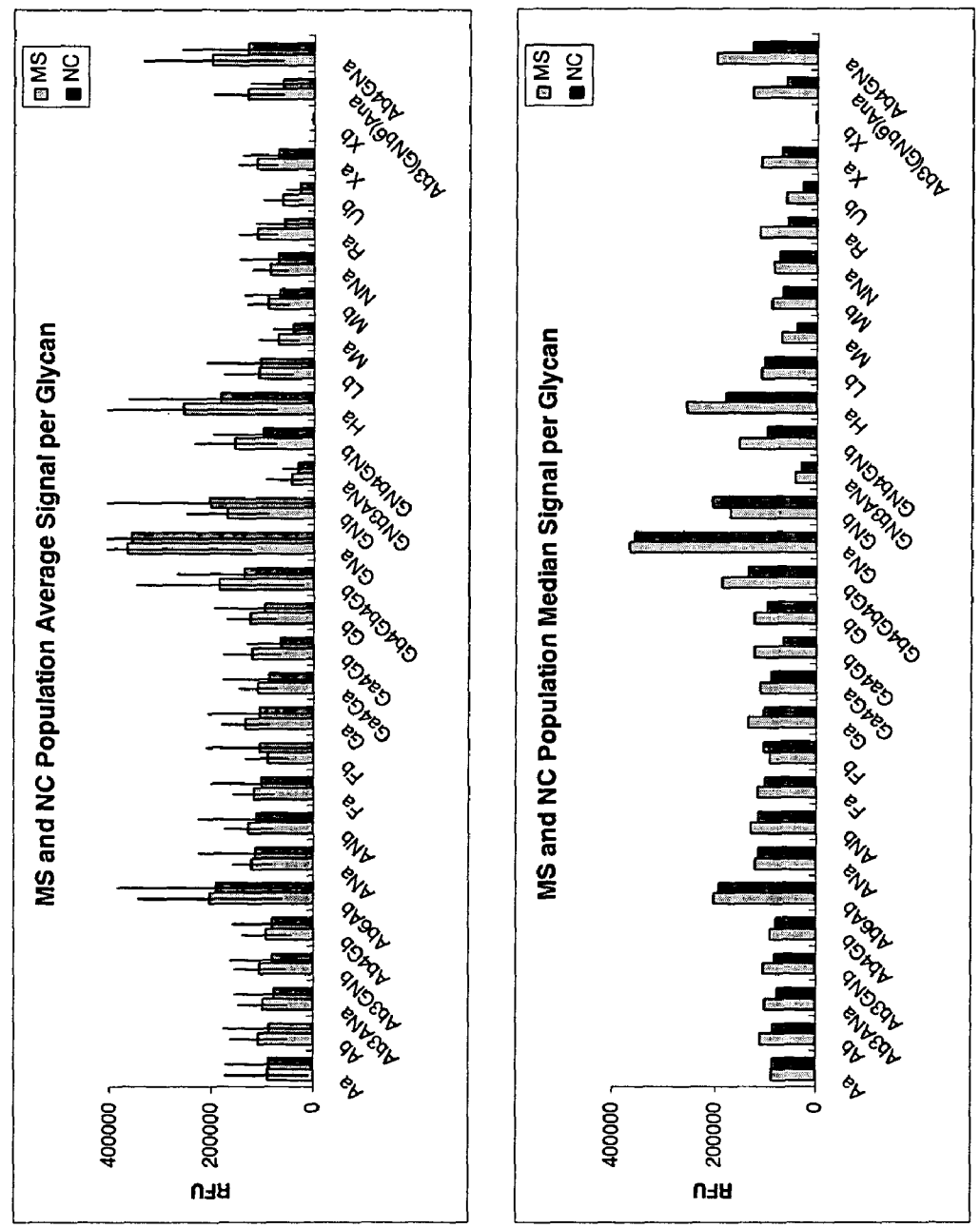
FIG. 5 shows the average and median signal for anti glycan antibodies to various glycans from sera extracted from MS patients versus normal control sera. The glycans structures are presented in LINEARCODE® syntax.

A comparison between the average and median values of anti-carbohydrate antibodies in the MS and normal populations reveals significant differences between the samples from the MS patients and the samples from the normal population, see FIG. 5. One example of a major difference observed between the two groups is the average signal to the glycan Ga4Gb. A t-test showed that the difference is highly statistically significant (α=0.05; p<0.001). Another example is Ab3(GNb6)ANa, (α=0.05; p<0.001). There are significant differences between the medians of signals of MS and normal population regarding antibodies bound to the following glycans: Glc (α), Glc (α 1-4) Glc (α), Glc (α 1-4) Glc (β), Glc (β), Gal (β), Glc (β 1-4) Glc (β 1-4) Glc (β), GlcNAc (β 1-4) GlcNAc (β), L-Araf (α), L-Rha (α), Gal (β1-3) [GlcNAc (β1-6)] GalNAc (α), Gal (β 1-4) GlcNAc (α), Gal (β 1-3) GalNAc (α), Gal (β 1-3) GlcNAc (β), GlcA (β), GlcA (β), Xyl (α). The signal from bound antibodies in MS group is higher then the signal in the normal control group.

Figure 6:
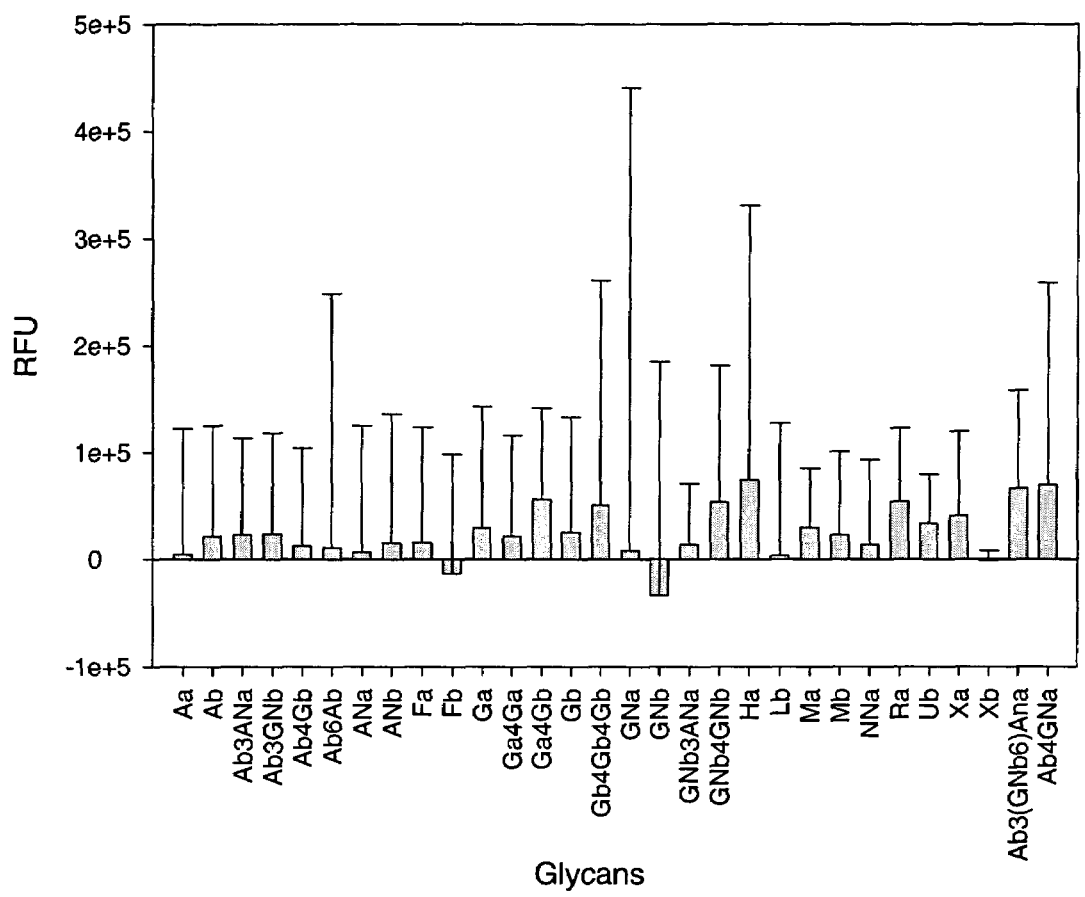
FIG. 6 is a graph showing the differences between average signals of MS and healthy individuals, bars represents standard deviation. The glycans structures are presented in LINEARCODE® syntax.

FIG. 6 presents the difference between the average binding values of anti-glycan antibodies between the populations.

EXAMPLE 2

Differences in the Levels of Anti-Glc (α), and Anti-Glc (α 1-4) Glc (α), a IgM Antibodies in the Serum Between MS Patients in Attack, Stable MS Patients and Healthy Population A glycan array was used to search for biomarkers among the human serum glycan binding antibody repertoire to differentiate between a healthy population and a group of Multiple Sclerosis (MS) patients, and between MS patients in exacerbation and remission stages. This example demonstrates that two IgM antibodies, anti-Glc (α) and anti-Glc (α 1-4) Glc (α), are found at significantly higher levels in MS patients than in healthy people (sensitivity and specificity of 60% and 93%, respectively), and in MS patients in an exacerbation stage relative to patients in a remission stage (sensitivity and specificity of 89% and 71%, respectively). Also provided is an anti-glycan antibody profile for a healthy population, including a range of variation during a 13 week interval.

The temporal stability of antiglycan antibodies profile over 13 week in apparently healthy individuals was high. The low levels of of anti-Glc (α) and anti-Glc (α 1-4) Glc (α) IgM in a normal population, and their high level in MS patients, and the high temporal stability of anti glycan antibodies suggests that this anti Glc (α) and anti-Glc (α 1-4) Glc (α)IgM can serve as biomarker for early diagnosis, early prescribing of drugs, monitoring drug effects and early detection of attacks.

All serum samples were tested using GlycoChip® (Glycominds Ltd., Lod, Israel). The glycans were covalently bound to the plastic surface through a linker as previously described (WO02/064556). A list describing the mono-and oligosaccharides tested is provided in Table 1.

Blood samples were obtained from apparently healthy blood donors under an informed consent protocol approved by the Helsinki Human Studies Ethical committees of the Belinson Medical Center in Tel-Aviv, Israel, and Carmel Medical Center in Haifa, Israel. Blood samples were collected from MS patients admitted to the Multiple sclerosis Clinic in Carmel Medical Center in Haifa, Israel. The blood samples were collected in evacuated silicon coated tubes containing gel for the separation of sera from the blood clot (Estar Technologies). After coagulation of the blood, serum was separated by centrifugation and collected. Samples were stored frozen at −25° C. until used.

The volume of all solutions added to the glycan array was 10 μl/well. The sera were diluted (1:20; saturating concentration) in 0.15M Tris-HCl pH 7.2, 0.085M $Mg_2SO_4$, 0.05% Tween 20 (TBST) containing 1% BSA (Sigma), dispensed into glycan array plates using a Tecan Genesis Workstation 200 automated handling system, and incubated for 60 min at 37° C. The plates were then washed with 250 μL/well Phosphate buffered Saline with 0.05% Tween 20 (PBST, Sigma) in an automatic plate washer (Tecan, PowerWasher™). At this point the following reagents, diluted in TBST with 1% BSA, were added using a Multidrop 384 dispenser (Thermo Labsystems) and incubated for 60 min at 37° C.: for IgG, IgA, and IgM determination—the respective sub-class specific biotinylated goat anti-human Ig antibody (Jackson, Pa., USA) at 2.8 μg/ml, 3 μg/ml, and 0.9 μg/ml, respectively; for total Ig determination—biotinylated Protein A (1 μg/ml, ICN Biomedicals). Following washing with PBST, Streptavidin-conjugated europium (0.1 μg/ml) diluted in TBST with 1% BSA was added to each well followed by incubation for 30 min at 37° C. in the dark, and washing with PBST. Delfia™ enhancement solution was then added to the wells and the plates were incubated for 30 to 45 min in the dark at room temperature. The fluorescence of the wells was read with a Victor 1420 (Wallac, Finland) plate reader using time resolved fluorescence settings of 340/612 nm (Excitation/Emission).

Differences in the Levels of Anti-Glc (α) and Glc (α 1-4) Glc (α) a IgM Antibodies in the Serum Between MS Patients in Attack, Stable MS Patients and Healthy Population Serum samples were obtained from MS patients admitted to an outpatient clinic for regular examination after they signed informed consent forms. The patient group was 80% female, approximately reflecting the gender ratio in the general MS population. In accordance with published data (Ritchie et al., J. Clin. Lab. Anal. 12:363-70, 1998), significantly higher levels of IgM (but not IgG or IgA) antibodies were observed in sera from both healthy and MS women as compared to men (not shown). The analysis was therefore limited to the female MS and healthy sub-populations only. Sera of MS patients were initially screened on 54 glycans (Table 1) for the presence of IgG, IgM and IgA anti-glycan antibodies with the purpose of identifying markers that would confirm patients with single acute demyelinating events as MS, and markers that would distinguish between patients during the exacerbation and remission stages of the disease. The experiment was repeated twice using five out of the 54 glycans against which some differences between the groups were found in the initial round.

A reproducible and statistically significant difference in the levels of IgM anti Glc (α) and anti-Glc (α 1-4) Glc (α)antibodies was found between the healthy and MS groups (FIG. 7A), but no significant differences in IgG or IgA levels were found in these studies (not shown). In sera of both groups of MS patients the levels of IgM anti-Glc (α) and anti-Glc (α 1-4) Glc (α) were significantly higher than in the healthy population. An arbitrary set optimal cut-off value (the 97% percentile signal of the "healthy" population) was used to identify positive samples above—and negative samples—below the cut-off value. Thus, anti-Glc (α) binding signals identified correctly 19 out of 42 MS samples (45% sensitivity) and 42 out of 44 apparently healthy sera samples (96% specificity). Measurement of anti-Maltose binding identified correctly 48% of the MS sera and 95% of the apparently healthy sera samples. Defining positive as a sample which signal is above the cut-off value in either the anti-Glc (α) or Glc (α 1-4) Glc (α) assays, improves the sensitivity to 60%, and leaves specificity at 93% (Table 2). The differential distribution of anti-Glc (α) and anti-Glc (α 1-4) Glc (α) antibodies in patients during the exacerbation and remission stages of the disease was significantly higher levels in the former group (FIG. 7B). No difference was found between untreated patients or patients treated with interferon-β (not shown). Using as a cut-off of the 80% percentile of the "stable" MS population, it was determined that anti-Glc (α) binding signals identified correctly 15 out of 18 "attack" samples (83% sensitivity), 19 out of 24 "stable" samples (79% specificity relating to stable as symptom free), and 42 out of 44 "healthy" samples (95% specificity). Measurement of anti-Maltose binding identified correctly 72% of the attack sera, 79% of the "stable" sera, and 97% of the "healthy sera". Defining a positive as a sample which signal is above the cut-off value in either the Glc (α) OR Maltose assays, results in sensitivity of 89%, and specificity of 71% and 95% relative to "stable" or "healthy" samples, respectively (Table 3). The high specificity and sensitivity of the anti-Glc (α) and anti-Glc (α 1-4) Glc (α) IgM antibodies make them an efficient tool for early diagnosis and definition of MS patients. The fact that the levels of these antibodies in MS attack situation are much higher then in stable situation make them a tool for early identification and prediction of attacks in relapsing remitting MS patients.

Figure 8:
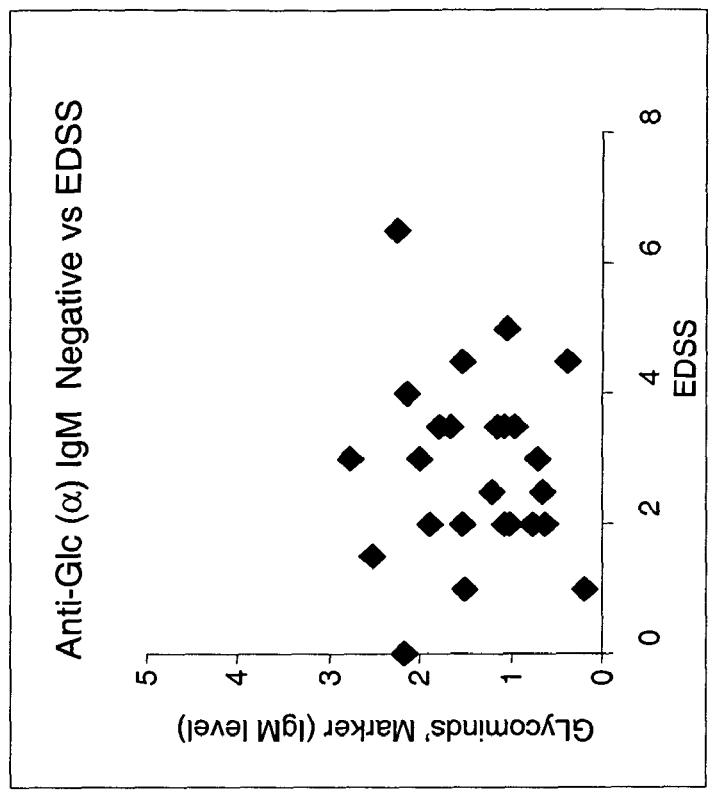
FIG. 8 is a graph showing the correlation between relative fluorescence from adhesion of anti Glucose alpha IgM antibodies in anti Glc ($\alpha$) positive MS patients (left box) negative MS patients (right box) samples and their EDSS levels.
Figure 8:
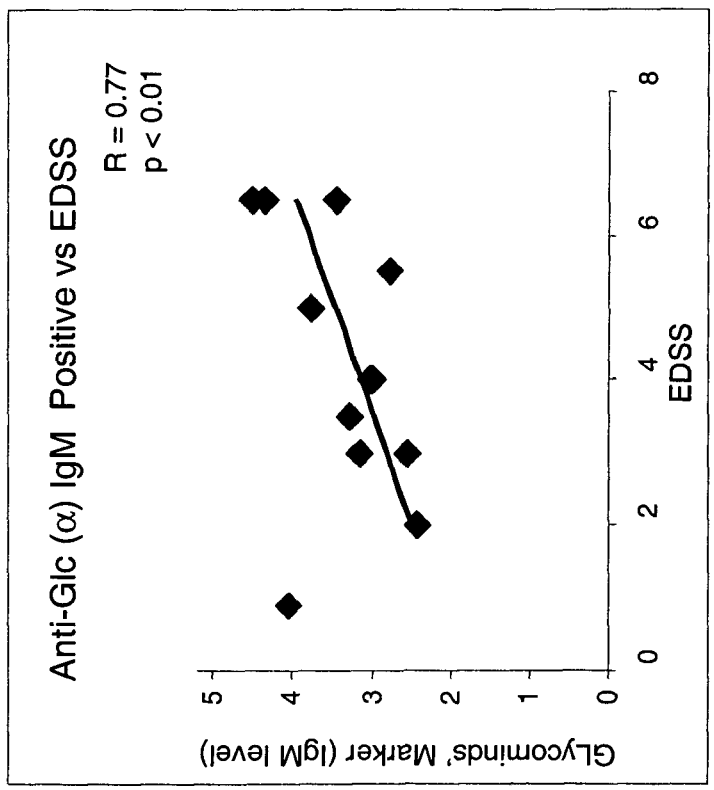

A high correlation between IgM anti-Glc (α)antibody serum levels in female, clinically diagnosed (relapsing-remitting) MS patients, who defined positive for having IgM anti-Glc (α)antibody (as described above), and the women's EDSS (Expanded Disability Status Scale) score was observed, see FIG. 8, left box. There was no correlation between EDSS and the IgM anti-Glc (α)antibody levels in serum for females, clinically diagnosed (relapsing-remitting) MS patients, who defined negative for having IgM anti-Glc (α) antibody, see FIG. 8 left box. The high correlation indicates that the levels of IgM anti-Glc (α) in serum can act as a molecular surrogate biomarker for evaluation the activity of the disease.

Temporal Range of Anti-glycan Antibody Levels

Figure 9:
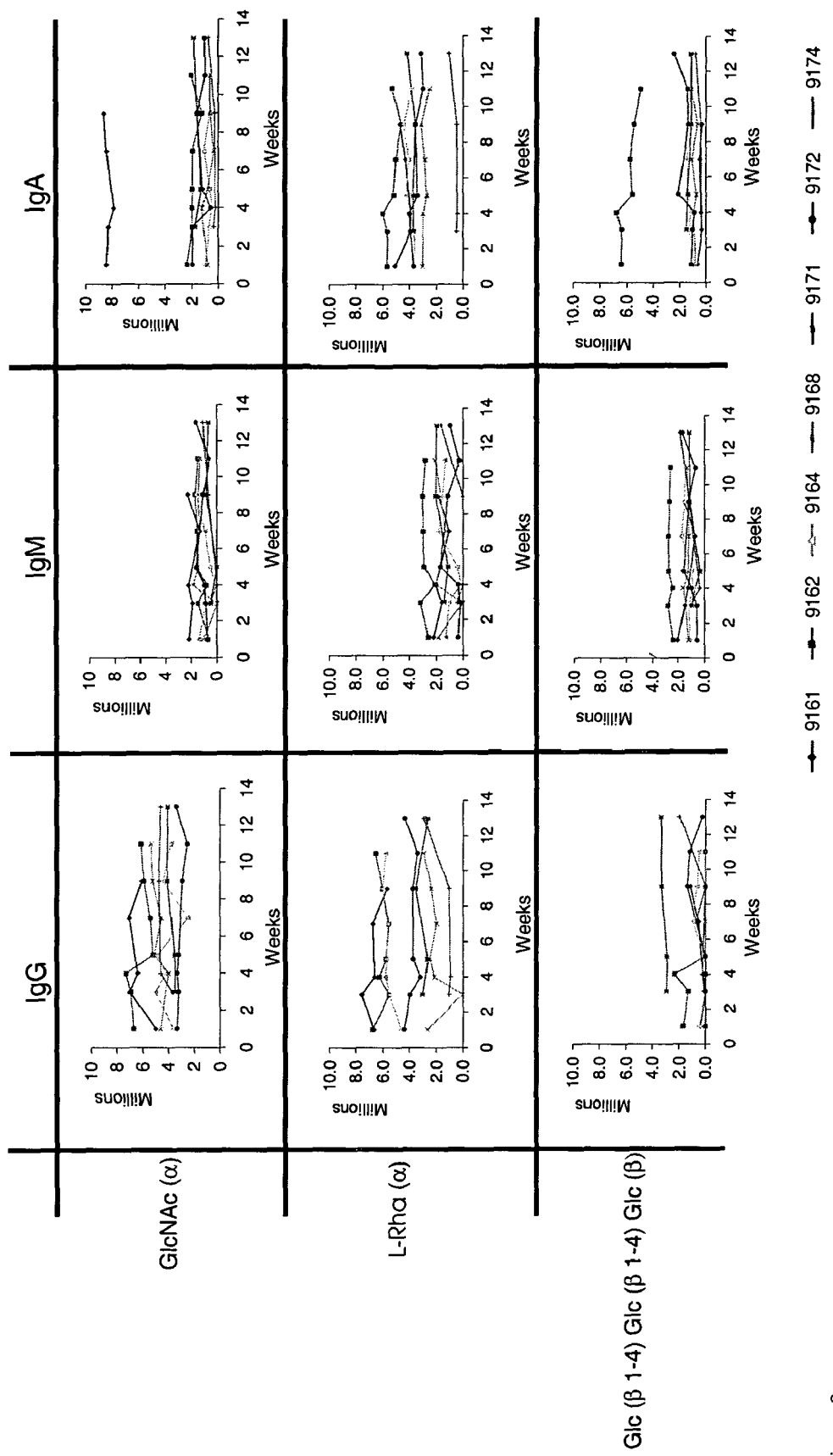
FIG. 9 is a graph showing the temporal stability of the signal from binding of IgM, IgG and IgA anti glycan antibodies over 13 weeks in 7 healthy individuals.

When considering any biological parameter for the use as a surrogate biomarker, it is obviously a prerequisite that the biomarker is not variable in time in the normal population. Thus, the serum levels of IgG, IgA, and IgM anti-L-Rha (α), anti-GlcNAc (α), and -anti Glc (β 1-4) Glc (β 1-4) Glc (β) (β Cellotriose), antibodies in seven healthy volunteers were followed for 13 weeks (FIG. 9). In general, the serum antibody concentrations were found to vary between the different individuals, but to be quite stable over time. For example, sera #9161 and #9162 have extremely high and temporally stable relative levels of IgA anti-GlcNAc (α) and Glc (β 1-4) Glc (β 1-4) Glc (β)antibodies, respectively, but relatively normal levels of IgA anti L-Rha (α)antibodies and IgG and IgM antibodies. When changes in antibody level do occur they are frequently gradual and continue over several weeks (e.g. serum #9162; IgA anti-Glc (β 1-4) Glc (β 1-4) Glc (β)), but can also be sudden, e.g. serum #9172; IgM anti-L-Rha (α), which suddenly increases between week four and five and then again slowly returns to its basic level.

EXAMPLE 3

Anti-glycan Antibody Profile (AGAP) in a Normal Human Population

Figure 11:
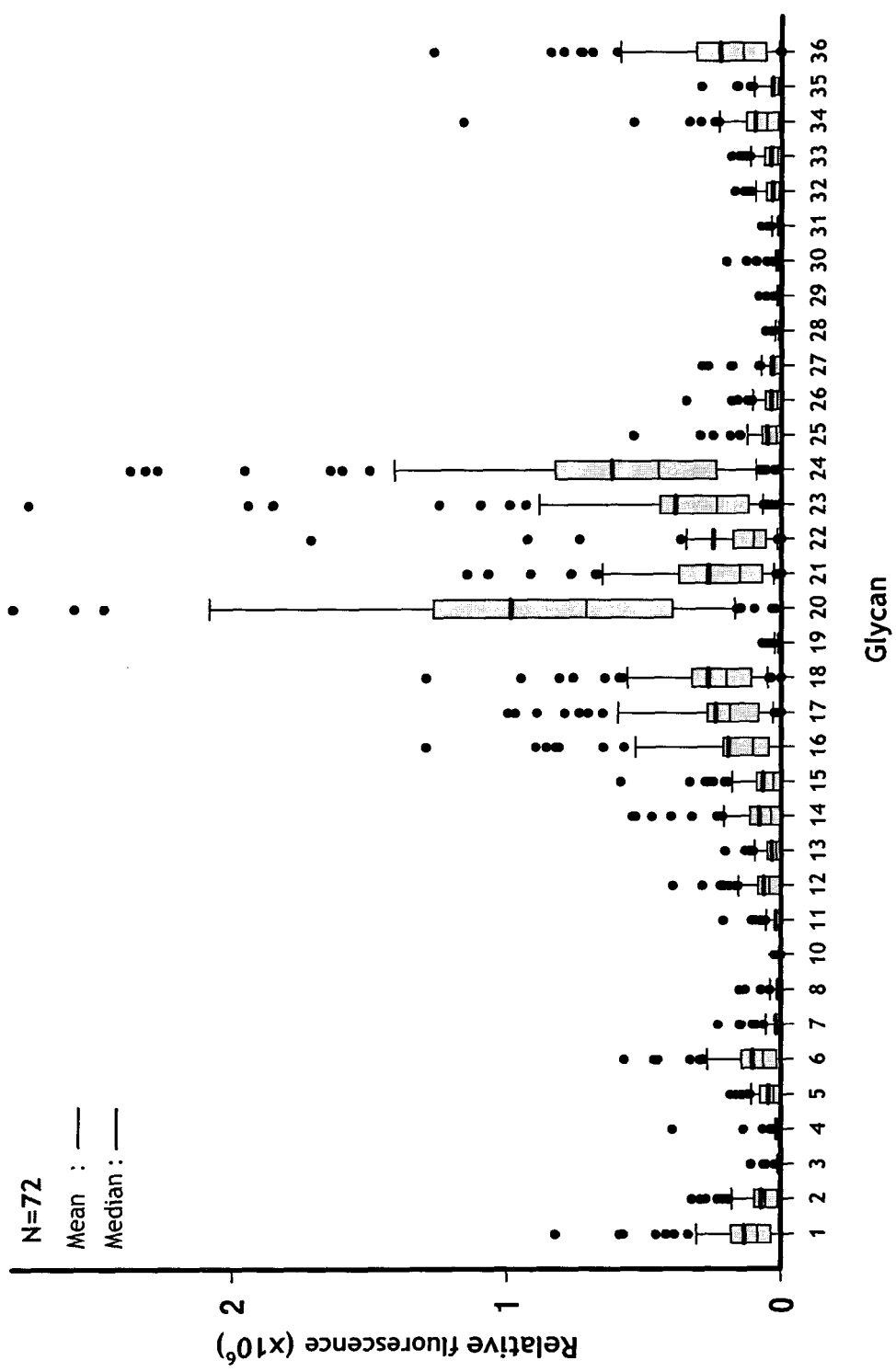
FIG. 11 shows the glycan binding profile of a healthy human population. Anti-carbohydrate antibody binding to assorted glycans (see Table 5 for glycan structures) in serum samples from 72 individuals as measured with biotinylated Protein A. Each dot represents the average of two experiments, each done in quadruplicate. The box includes signals of 50% of the population. The thick and thin lines in the box represent the mean and median values, respectively. The boundary of the box closest to zero indicates the 25th percentile, and the boundary of the box farthest from zero indicates the 75th percentile. Whiskers above and below the box indicate the 90th and 10th percentiles. The level of nonspecific signal measured was defined empirically; Glycans against which antibody levels were found to be relatively low and highly variable between experiments were designated to define background level (not shown). The average signal value for these glycans was calculated and subtracted from the signal obtained for each serum sample and particular glycan. The average background was $3 \times 10^5$ RFU. TBST is Tris-buffered Saline with Tween-20 (see Experimental Protocol).
Figure 12:
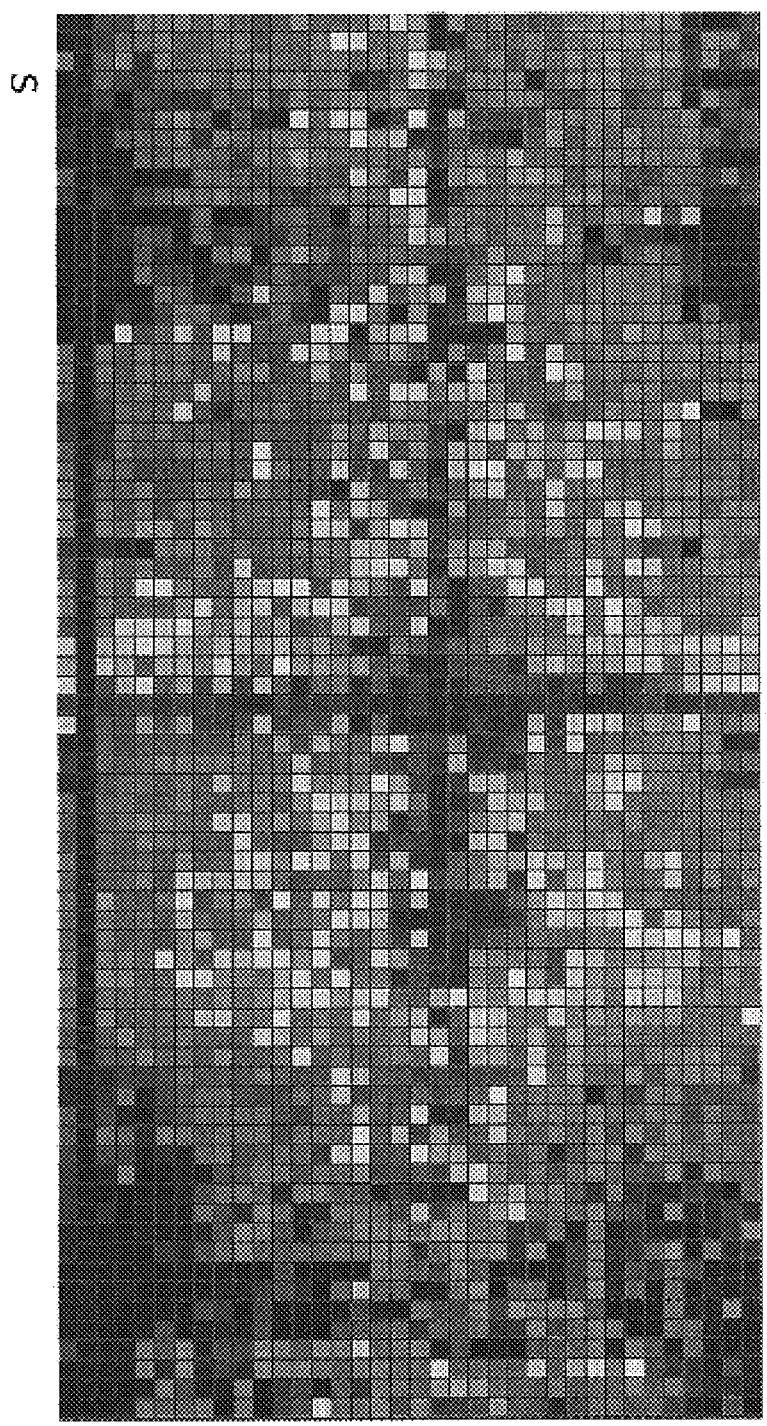
FIG. 12 shows the signals of individual sera against a series of glycans. The anti-glycan antibody binding measured in relative fluorescence units (RFU) were transformed using a histogram equalization-like method which employs a monotonic, non-linear mapping. This way, the RFU values were re-assigned to range between 0 (blue) and 255 (red). The data were clustered using a simulated annealing algorithm.
Figures 15A, 15B, 15C:
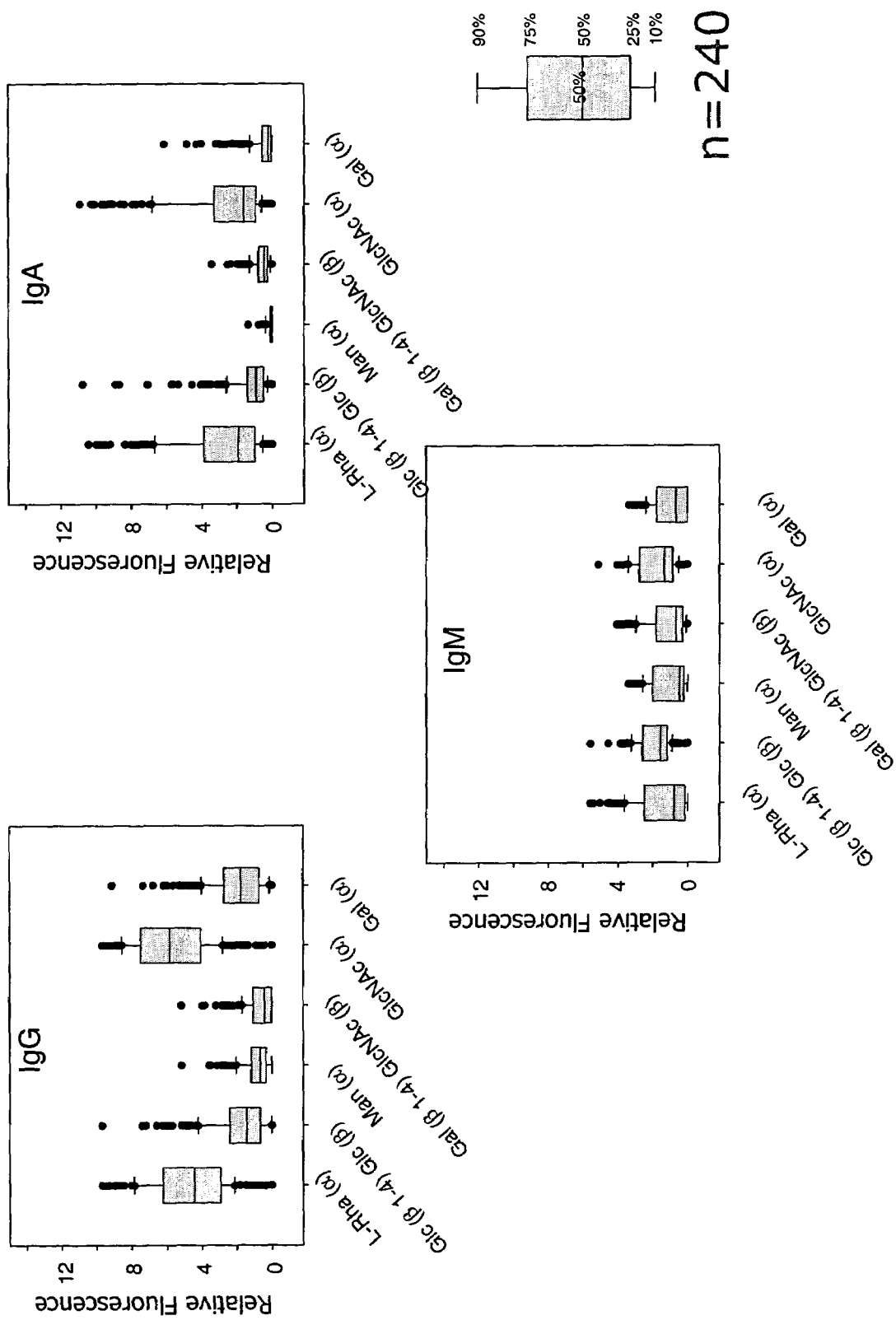
FIGS. 15A-15C are graphic representations of bindings of IgG, IgA, and IgM isotypes of healthy individuals to the indicated glycans.

Total Ig antibody binding (as detected with Protein A) of 72 individual sera to 34 mono- and oligosaccharides (FIG. 11 and Table 5), and IgG, IgA, and IgM binding of 200 sera to six mono- and oligosaccharides (FIG. 15A-C) was determined.

The strongest signals were recorded for antibodies against GlcNAc (α) and L-Rha (α), while lower levels were observed against β4-linked oligosaccharides of glucose, GlcNAc (β), GlcNAC (β 1-4) GlcNAC (β), Gal (α) and Gal (a 1-3) Gal (β 1-4) GlcNAc (β). This is in good agreement with previously published data showing the distribution of anti-glycan antibodies in a commercially available human serum pool (WO02/064556). The AGAP of subclasses IgG and IgA were similar to the total Ig AGAP, while that of IgM was lower and more uniform among the different glycans. The anti-glycan antibodies of the population tended to fit a lognormal distribution see FIG. 15A-15C. It is evident that considerable variation in anti-glycan antibody levels exists between individuals within the population examined, a fact that suggests the existence of individual AGAPs, but limits the search of markers to anti-glycan antibodies present at low amounts.

Figure 13:
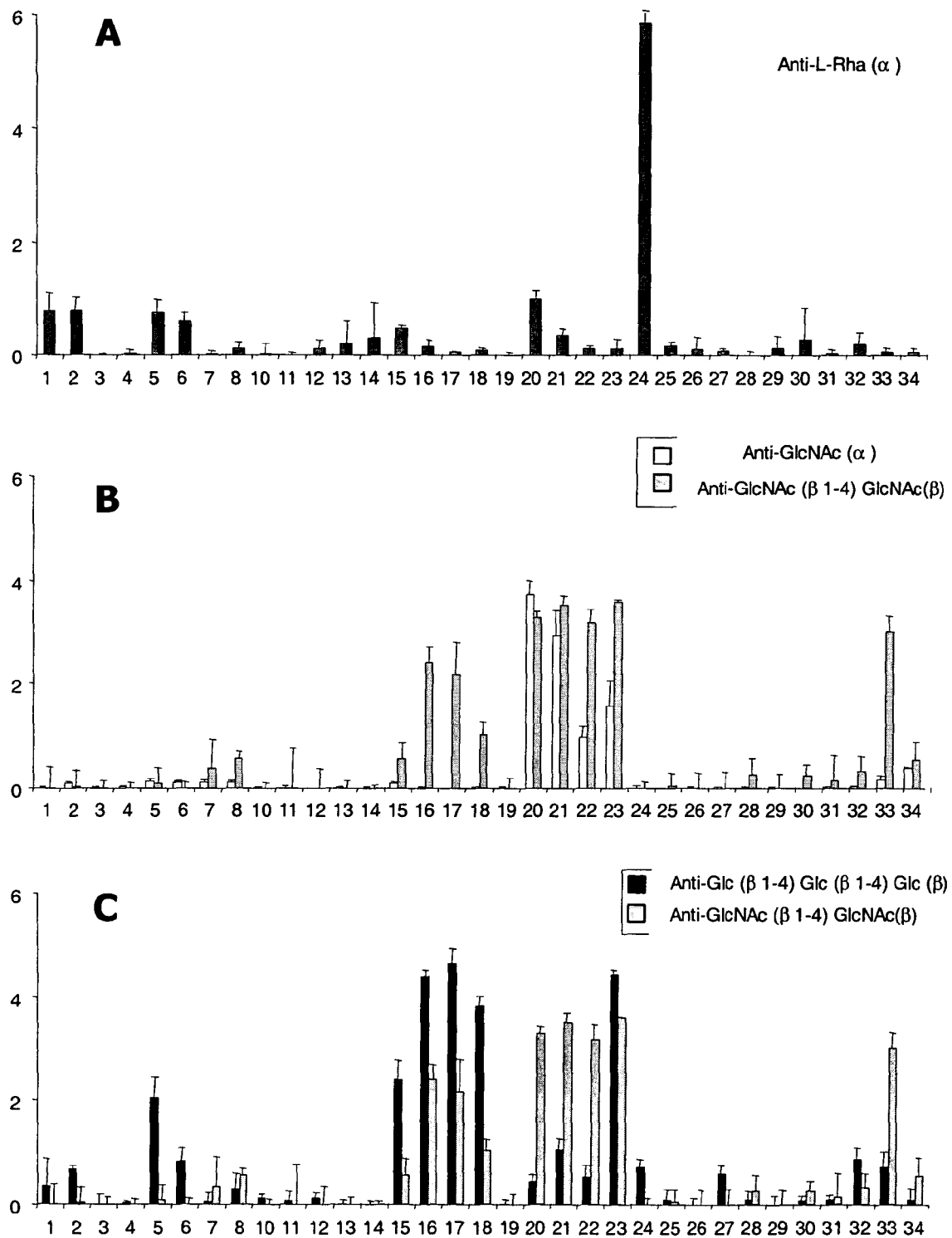
FIGS. 13A-13C show the binding profile of affinity purified (A) anti-L-Rha ($\alpha$) (B) anti-GlcNAc ($\alpha$) and anti-GlcNAc ($\beta$ 1-4)GlcNAc ($\beta$) and (C) anti-Glc ($\beta$ 1-4) Glc ($\beta$ 1-4) Glc ($\beta$) and anti-GlcNAc ($\beta$ 1-4) GlcNAc ($\beta$) antibodies to an array of 33 glycans. The glycans structures are described in Table 5. Amount of antibody bound was measured using biotinylated Goat Anti-human IgG antibody.
Figure 14A:
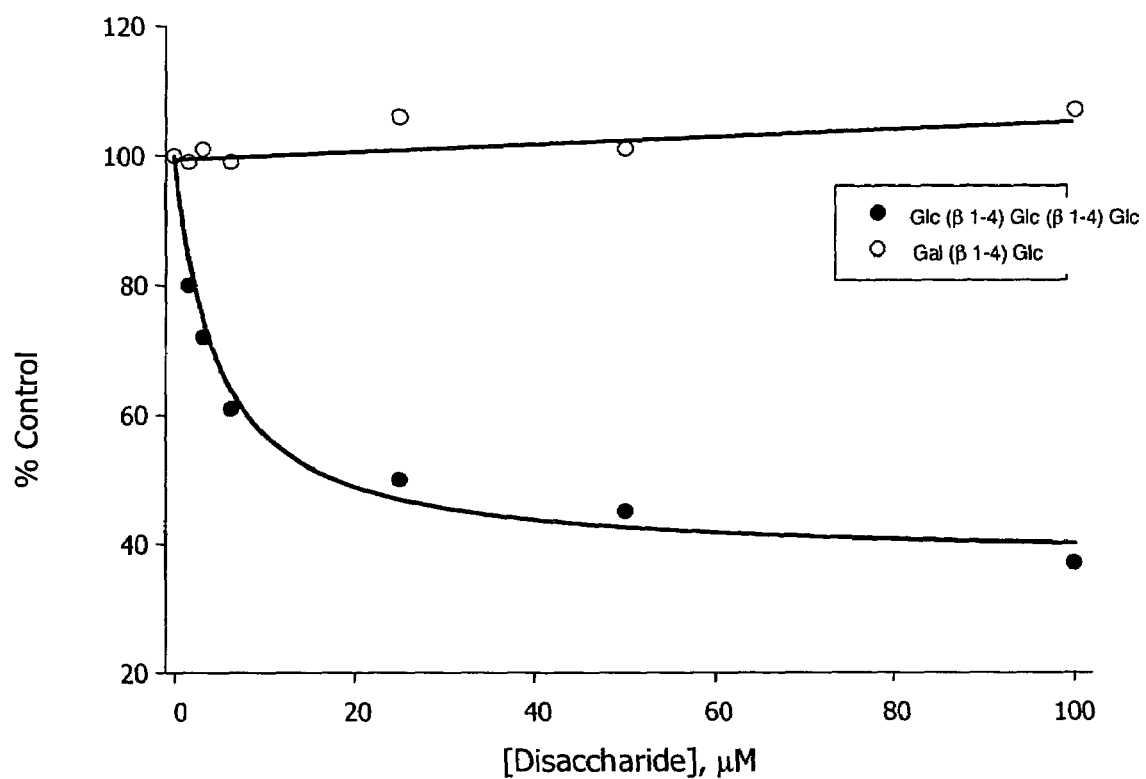
FIGS. 14A and 14B show the specificity of anti-Glc ($\beta$ 1-4) Glc ($\beta$ 1-4) Glc ($\beta$) antibody. (A) Competitive inhibition of anti-Glc ($\beta$ 1-4) Glc ($\beta$ 1-4) Glc ($\beta$) antibody binding. Inhibition of binding of affinity purified anti-Glc ($\beta$ 1-4) Glc ($\beta$ 1-4) Glc ($\beta$) antibody to p-amino phenyl-$\beta$-Glc ($\beta$ 1-4) Glc ($\beta$ 1-4) Glc ($\beta$) immobilized to the well surface as a function of Glc ($\beta$ 1-4) Glc ($\beta$ 1-4) Glc or Gal ($\beta$ 1-4) Glc concentration. The amount of antibody bound was measured using biotinylated Goat Anti-human IgG antibody. (B) Binding of anti-Glc ($\beta$ 1-4) Glc ($\beta$ 1-4) Glc ($\beta$) (A) and anti-L-Rha ($\alpha$) (B) antibodies to their cognate saccharide after incubation with crystalline or amorphous cellulose. The amount of antibody bound was measured using biotinylated Goat Anti-human IgG antibody.
Figure 14B:
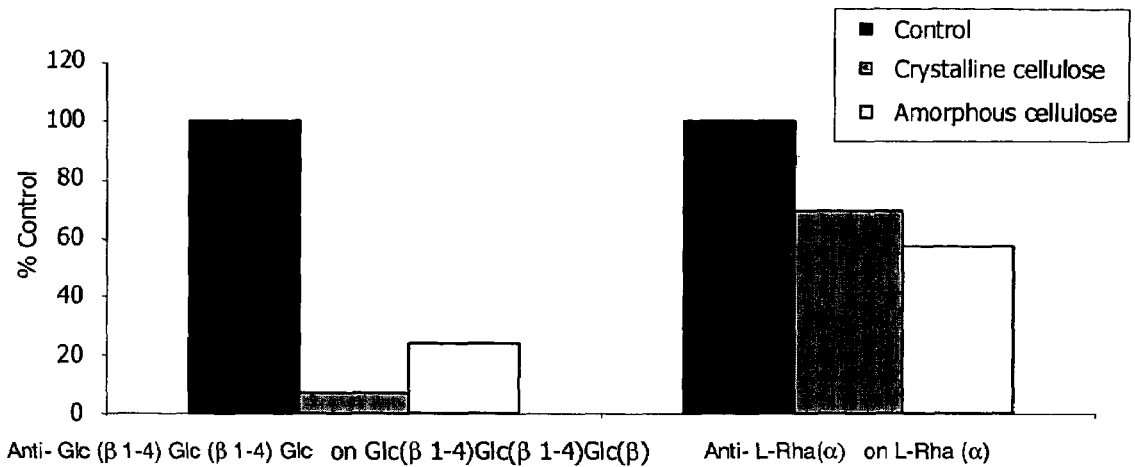

Glycans immobilized on beads affinity beads have also been used to purify antibodies to β4-linked oligosaccharides of glucose and L-Rha(α). Their binding profile and specificity are described in FIGS. 13, 14A and 14B.

EXAMPLE 4

Use of Anti-glycan Antibodies to Differentiate Between High Risk Atherosclerosis Patients with Vulnerable Plaques and Low Risk Atherosclerosis Patients with Stable Plaques Levels of anti-glycan antibodies in the sera of atherosclerosis patients with vulnerable plaques were compared to levels of glycan antibodies in serum of atherosclerosis patients with stable plaques, as well as individuals without atherosclerosis.

Atherosclerosis is a major cause of morbidity and mortality in developed countries. It is a systemic disorder of blood vessel walls that leads to the development of atherosclerotic plaques on the blood vessel walls. Some of these plaques later become vulnerable to rupture, causing blood clots leading to heart attacks or stroke.

The main components of atherosclerotic plaques are proteoglycans, lipids, muscle cells, and white blood cells (T-cells and macrophages). In addition, atherosclerosis is perceived as an autoimmune disease where one of its initiators is cross reactivity between antibodies to bacterial antigens and the antigens on blood vessel walls.

An important point in the development of atherosclerosis is the shift from Stable Plaques (SP), which are associated with low risk, to inflamed Vulnerable Plaques (VP), which are associated with high risk. Differentiating between SP and VP is clinically problematic, as a conclusive distinction can be made only a by post-mortem autopsy.

Serum samples where supplies by Dr. Jacob George from the cardiology department in the Tel Aviv Medical Center, Israel. All patients were non-diabetic males with an age range from 30 to 69. 39 serum samples of patients from the following types were tested:

Unstable Angina—13 Atherosclerosis patients characterized as having Acute Coronary Syndromes (Q wave or non Q wave myocardial infarctions). Both are considered to develop from rupture of vulnerable plaques. Members of the Unstable Angina group included acute coronary syndrome patients admitted with chest pain and ECG changes or cardiac marker elevation. They complained of recent onset (<3 days) of angina and were subjected to continued electrocardiogram (ECG) telemetric monitoring during admission. At least one episode of rest angina or an episode lasting more then 20 min during last 48 hr was detected, along with an increase in creatine kinase, MB levels or Troponin levels. Members of this group had undergone coronary angiography (catheterization), which documented the presence of coronary atherosclerosis.

Stable Angina—13 Atherosclerosis patients were characterized as having Stable Angina. Members of the Stable Angina group had undergone coronary angiography (catheterization) documenting the presence of coronary atherosclerosis. No ECG changes were detected, nor were increases in creatine kinase, MB levels or Troponin levels detected.

No plaques—13 Patients with normal coronary arteries. Members of the "No Plaques" group showed no evidence of coronary atherosclerosis following catheritization.

An anti-glycan antibody profile was obtained using GlycoChip™ arrays (Glycominds, Ltd., Lod, Israel, Cat No. 9100) constructed using procedures described in WO00/49412. All sera samples were tested using GlycoChip™ plates (Glycominds Ltd., Lod, Israel, Cat No. 9100), which contained an array of covalently attached mono and oligosaccharide in a reduced volume 384 well micro titer plate. The list of the mono and oligosaccharide displayed on the array as well as their serial numbers are described in Table 4.

Sera were diluted (1:20) in TBST dispensed into a GlycoChip™ plate using a Tecan Genesis Workstation 200 robot (10 μL/well) and incubated 30 min at 25 degrees Celsius. Each glycan and serum sample on the plate was tested 8 times.

The plates were washed with 250 μL/well of high salt buffer (0.15 M KNa pH 7.2, NaCl 2M, MgSO4 0.085M, 0.05% Tween20) in an automatic plate washer (Tecan, PowerWasher™). Ten μl/well of biotinylated goat anti-human IgG, IgM or IgA (Jackson, PA, USA), 1 μg/ml in TBST, was dispensed manually and the plates incubated for 30 min at 25° C. The plate was washed again with high salt buffer.

Streptavidin-conjugated Europium, Wallac, AD0062 (1 μl/ml, 10 μl/well) was added manually followed by incubation for 30 min at 25° C. in the dark. Washing of the plates with the high salt buffer was repeated. Delfia™ enhancement buffer, (Wallac, 730232, 10 μl/well) was added to the wells and the plates were incubated at least 30 min in the dark. The fluorescence of the wells was read with Victor 1420 (Wallac) using time resolved fluorescence settings Emi. 612 nm and Ext. 340 nm.

The glycan binding signal obtained for the "No plaque" group was used to calculate cut-off values for each glycan above which patients were considered to be positive. These cut-off values were defined as the average signal of the "No plaque" group plus one or two standard deviations. According to this definition a number of glycans were identified which had some degree of separating power between the patient groups (see below). "Separation" based on a certain glycan was defined as at least 50% (7/13) positive samples in the "Unstable angina" or "Stable angina" groups, and 2 or less positive samples in the "No plaque" group.

Figure 16A:
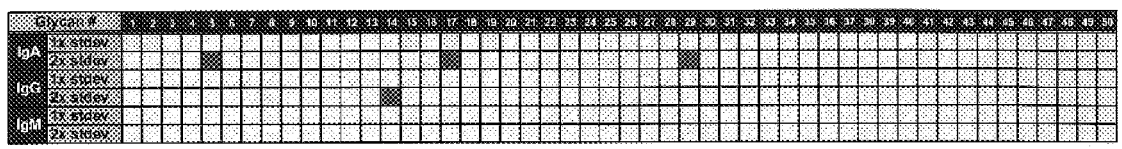
FIG. 16A is a matrix representation of glycans used to examine sera of atherosclerosis patients suffering from unstable or stable angina. Glycans against which significantly different antibody levels were measured in the different patient groups are labeled with filled squares. Glycans are listed in table 4.

FIG. 16A is a matrix representation of glycans used to examine sera of patients suffering from unstable or stable angina, the glycan structures are described in Table 4. Glycans against which significantly different antibody levels were measured in the different patient groups are labeled with filled squares. At the cut-off level of average plus two standard deviations "Separation" was achieved with IgA binding to two different glycans. One separated between IgG antibodies, but none separated between IgM antibodies.

The single glycans giving the best separations are presented below:

| Glycans | Result | Unstable Angina | Stable Angina | No Plaque |
|---|---|---|---|---|
| Ab | Positives | 7 | 5 | 0 |
|  | Negatives | 6 | 8 | 13 |
| Fb | Positives | 1 | 9 | 1 |
|  | Negatives | 12 | 4 | 12 |

Some glycans that were not defined as "separating" still gave some degree of separation. When used in combinations, separation could be improved beyond that of the single glycans. The glycans are presented below

| Glycans LinearCode | Result | Unstable Angina | Stable Angina | No Plaque |
|---|---|---|---|---|
| Aa | positives | 6 | 2 | 0 |
|  | negatives | 7 | 11 | 13 |
| Xb | positives | 1 | 6 | 0 |
|  | negatives | 12 | 7 | 13 |
| Fa | positives | 5 | 3 | 1 |
|  | negatives | 8 | 10 | 12 |
| A[3S]b | positives | 1 | 6 | 1 |
|  | negatives | 12 | 7 | 12 |
| GNb4GNb | positives | 5 | 0 | 1 |
|  | negatives | 8 | 13 | 12 |

Figure 16B:
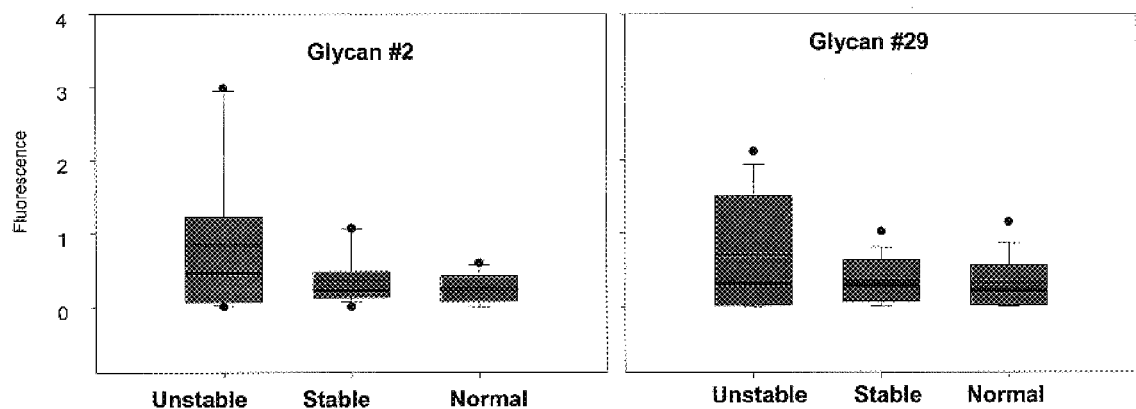
FIG. 16B is a graphic representation showing levels of antibodies against glycans #2 and #29 in the three patient groups; unstable, stable, and non atherosclerotic. The box includes signals from 50% of the population. The thick and thin lines in the box represent the mean and median values, respectively. The boundary of the box closest to zero indicates the 25th percentile, and the boundary of the box farthest from zero indicates the 75th percentile. Whiskers above and below the box indicate the 90th and 10th percentiles.

FIG. 16B is a graphic representation showing levels of antibodies against glycans #2 and #29 in the three patient groups. The box includes signals of 50% of the population. The thick and thin lines in the box represent the mean and median values, respectively. The boundary of the box closest to zero indicates the 25th percentile, and the boundary of the box farthest from zero indicates the 75th percentile. Whiskers above and below the box indicate the 90th and 10th percentiles.

Figure 17:
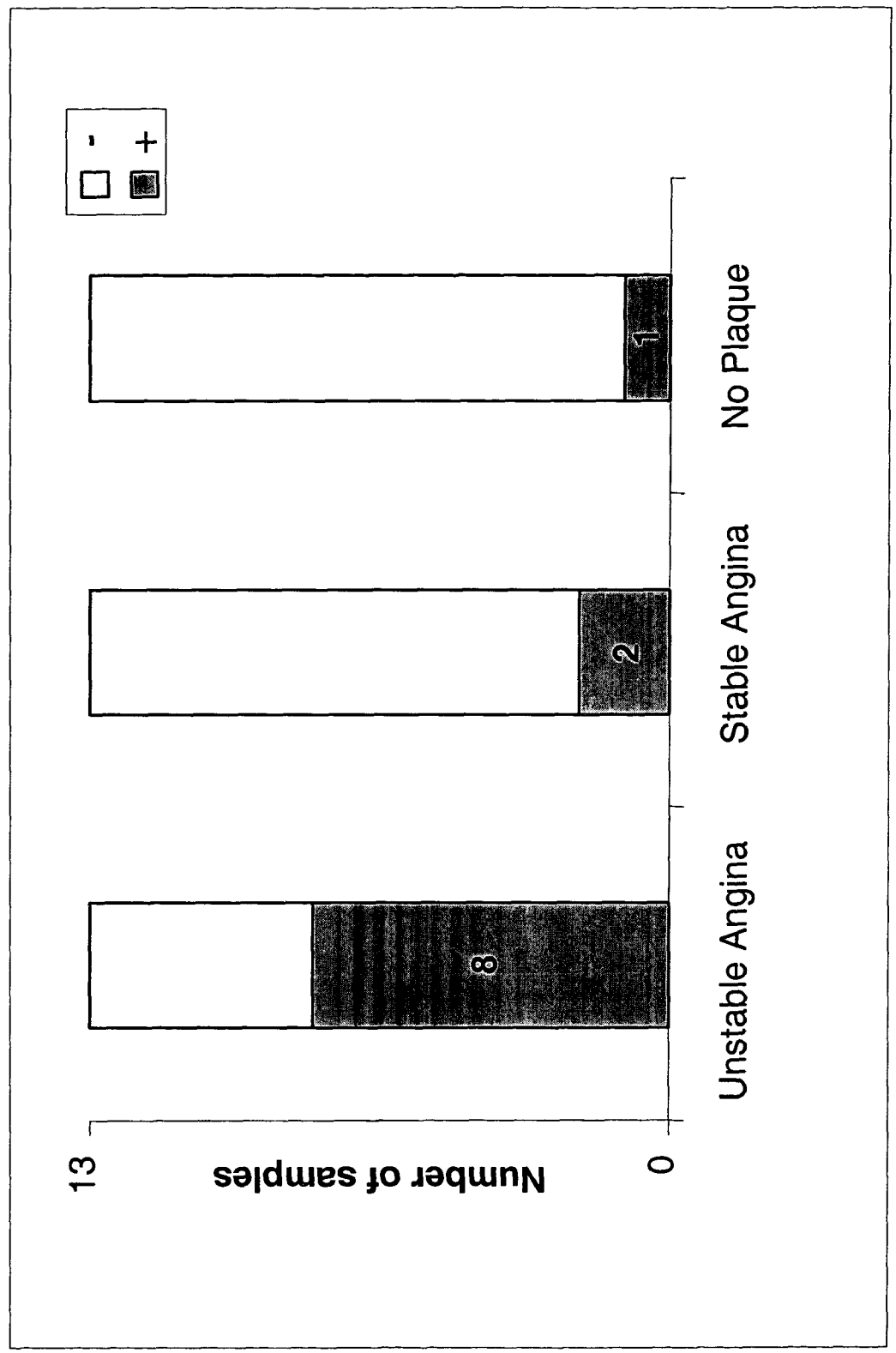
FIG. 17 is a histogram showing the number of samples in the three patient groups positive for anti-IgA antibodies against glycan #2 or glycan #29.

FIG. 17 is a histogram showing the number of samples in the three patient groups positive for anti-IgA antibodies against glycan #2 or glycan #29.

Figure 18A:
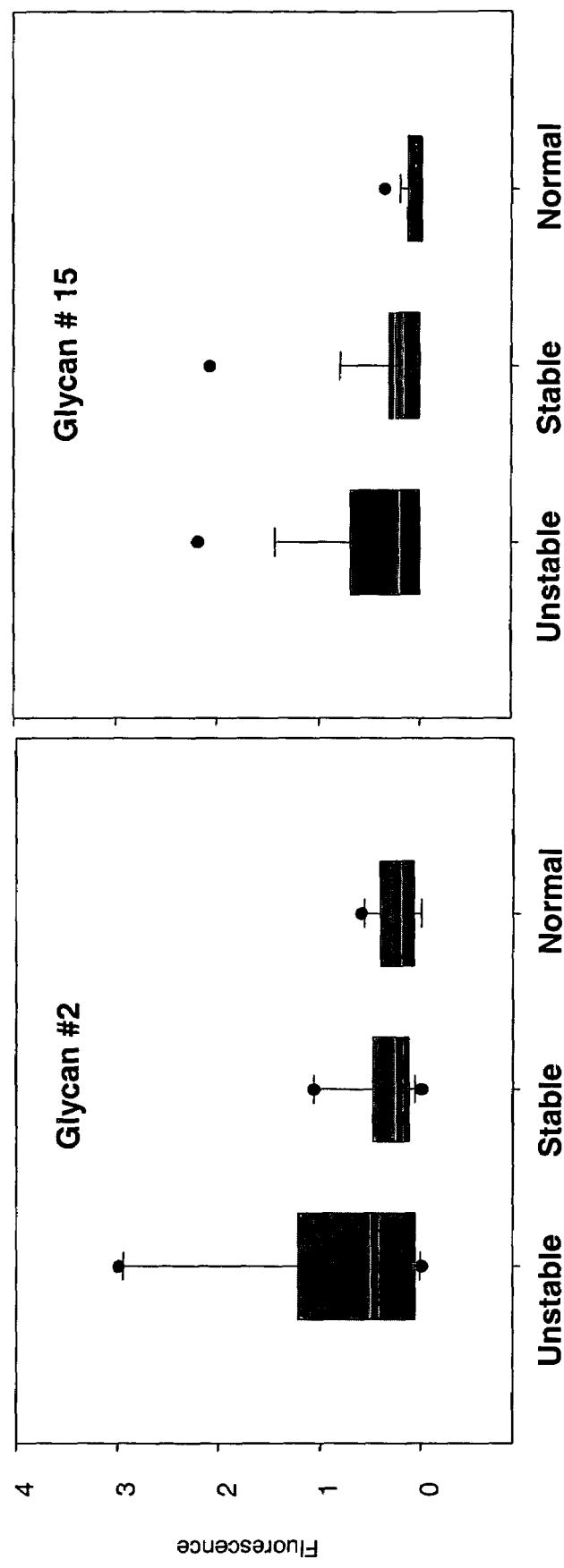
FIG. 18A is a histogram showing the distribution of antibody levels against glycans #2 and #15 in the three patient groups. The box includes signals from 50% of the population. The thick and thin lines in the box represent the mean and median values, respectively. The boundary of the box closest to zero indicates the 25th percentile, and the boundary of the box farthest from zero indicates the 75th percentile. Whiskers above and below the box indicate the 90th and 10th percentiles.

FIG. 18A is a histogram showing the distribution of antibody levels against glycans #2 and #15 in the three patient groups. The box includes signals of 50% of the population. The thick and thin lines in the box represent the mean and median values, respectively. The boundary of the box closest to zero indicates the 25th percentile, and the boundary of the box farthest from zero indicates the 75th percentile. Whiskers above and below the box indicate the 90th and 10th percentiles.

Figure 18B:
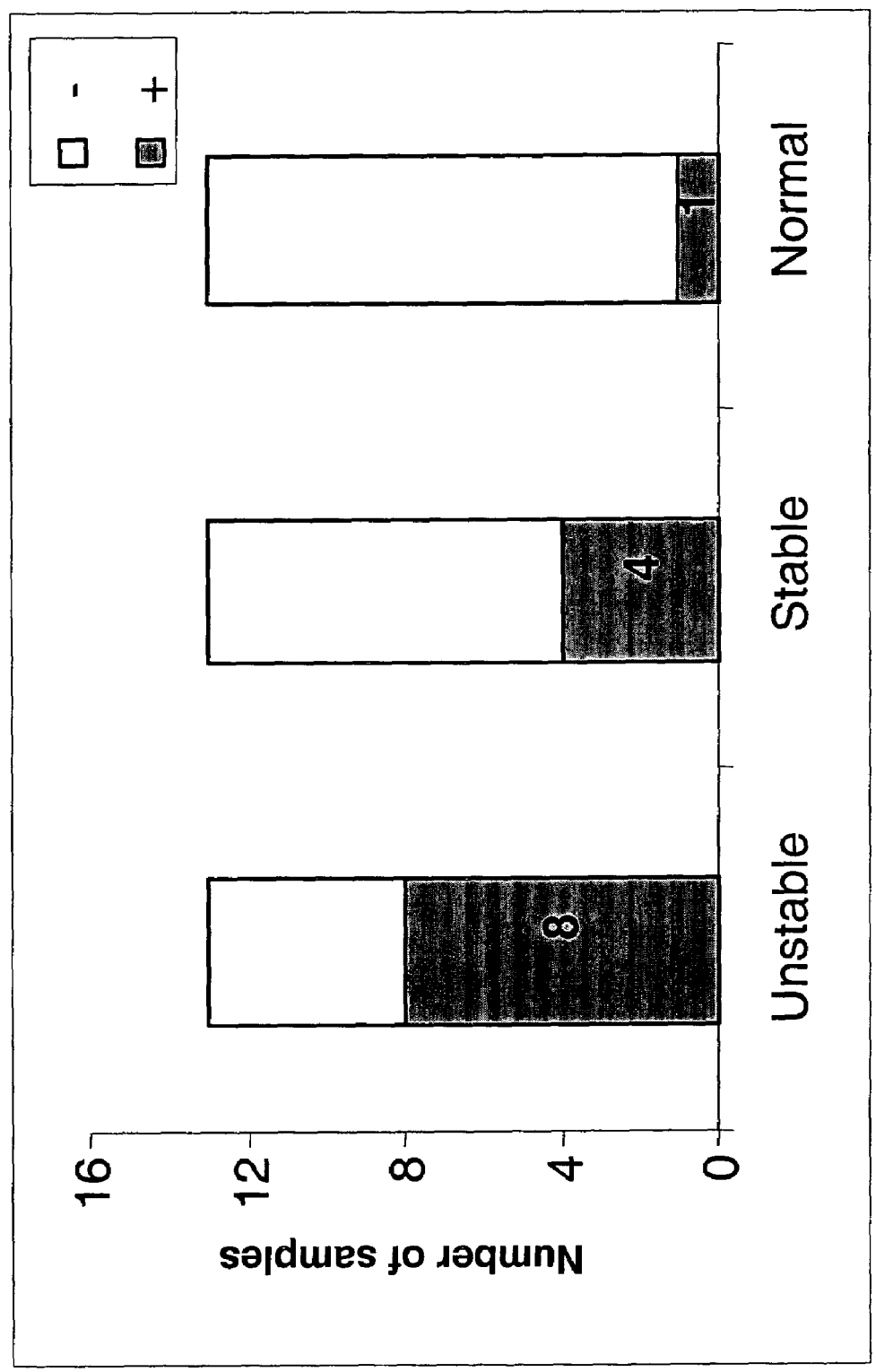
FIG. 18B is a histogram showing the number of samples in the three patient groups positive for anti-IgA antibodies against glycan #2 or glycan # 15.

FIG. 18B is a histogram showing the number of samples in the three patient groups positive for anti-IgA antibodies against glycan #2 or glycan #15. At the cut-off level of average plus one standard deviation, "Separation" was achieved with IgA binding to 6 different glycans. IgG and IgM antibody levels were not different in the three groups.

The separation obtained with combinations is shown below (Aa was used because the number of positive sample in the "Stable Angina" group was lower than using Ab, thus improving separation vis-à-vis the "Unstable Angina" group):

| Glycans LinearCode | Result | Unstable Angina | Stable Angina | No Plaque |
|---|---|---|---|---|
| Aa and GNb4GNb | Positive with one of the glycans | 8 | 2 | 1 |
|  | Negative with both | 5 | 11 | 12 |
| Aa and Ga4Ga | Positive with one of the glycans | 8 | 5 | 0 |
|  | Negative with both | 5 | 8 | 13 |

The specificity and sensitivity of the test to detect "Unstable angina" using Aa and GNb4GNb was thus 62% (8/13) and 88% (23/26), respectively.

Figure 19:
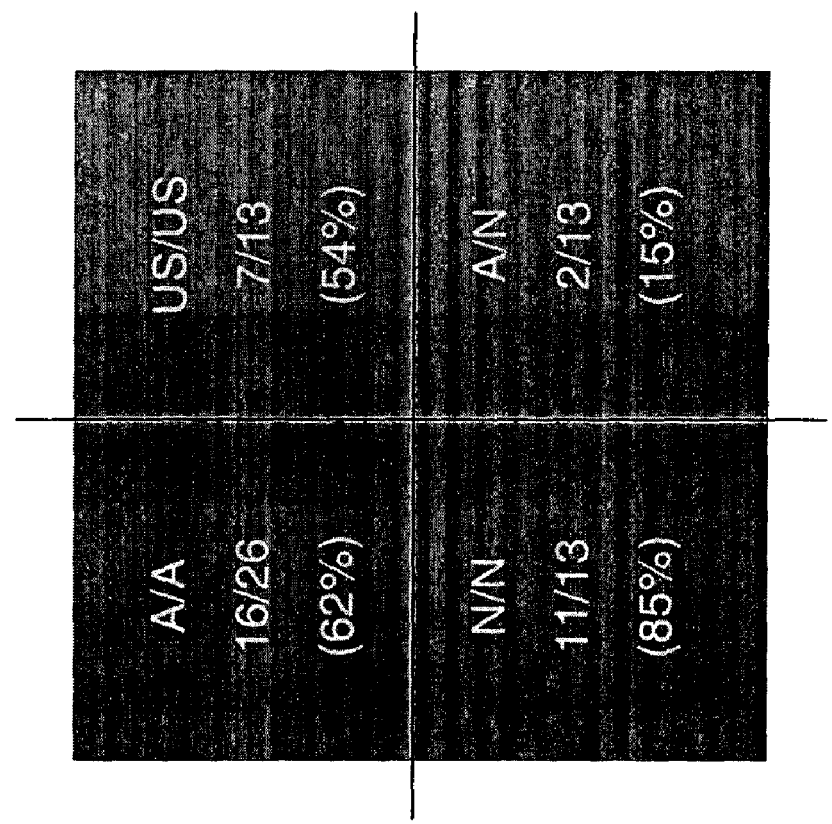
FIG. 19 is a graphical representation of the specificity and sensitivity based on anti-IgA antibodies levels against glycan #2, glycan #15, glycan #17, and glycan #49. A—Atherosclerosis; S—Stable; US—Unstable; NA—Non-Atherosclerosis.

A combination of three glycans, Aa, GNb4GNb, and Fb made it possible to determine specificity also for the "Stable angina" group 75% (9/13). This stems from the fact that Fb detects mostly "Stable angina". The specificity and sensitivity of the combined assay are summarized in FIG. 19.

These results demonstrate that a combination of glycans (Gal ($\alpha$), GlcNAc ($\beta$ 1-4) GlcNAc ($\beta$) andFu($\beta$)) can be used to successfully distinguish between stable and unstable angina populations with a specificity of 62% and sensitivity of 88%. This results show that it is possible to develop a biomarker based on glycan binding IgA antibodies that distinguishes between Unstable and Stable Angina patients.

EXAMPLE 5

Use of Anti-glycan Antibodies to Differentiate Between High Risk Atherosclerosis Patients with Vulnerable Plaques and Low Risk Atherosclerosis Patients with Stable Plaques Levels of anti-glycan antibodies in the sera of atherosclerosis patients with vulnerable plaques were compared to levels of glycan antibodies in serum of atherosclerosis patients with stable plaques, as well as individuals without atherosclerosis.

Atherosclerosis is a major cause of morbidity and mortality in developed countries. It is a systemic disorder of blood vessel walls that leads to the development of atherosclerotic plaques on the blood vessel walls. Some of these plaques later become vulnerable to rupture, causing blood clots leading to heart attacks or stroke.

The main components of atherosclerotic plaques are proteoglycans, lipids, muscle cells, and white blood cells (T-cells and macrophages). In addition, atherosclerosis is perceived as an autoimmune disease where one of its initiators is cross reactivity between antibodies to bacterial antigens and the antigens on blood vessel walls.

An important point in the development of atherosclerosis is the shift from Stable Plaques (SP), which are associated with low risk, to inflamed Vulnerable Plaques (VP), which are associated with high risk. Differentiating between SP and VP is clinically problematic, as a conclusive distinction can be made only a by post-mortem autopsy.

Serum samples where supplies by Dr. Jacob George from the cardiology department in the Tel Aviv Medical Center, Israel. All patients were non-diabetic males with an age range from 30 to 69. 72 serum samples of patients from the following types were tested:

Unstable Angina—24 Atherosclerosis patients characterized as having Acute Coronary Syndromes (Q wave or non Q wave myocardial infarctions). Both are considered to develop from rupture of vulnerable plaques. Members of the Unstable Angina group included acute coronary syndrome patients admitted with chest pain and ECG changes or cardiac marker elevation. They complained of recent onset (<3 days) of angina and were subjected to continued electrocardiogram (ECG) telemetric monitoring during admission. At least one episode of rest angina or an episode lasting more then 20 min during last 48 hr was detected, along with an increase in creatine kinase, MB levels or Troponin levels. Members of this group had undergone coronary angiography (catheterization), which documented the presence of coronary atherosclerosis.

Stable Angina—24 Atherosclerosis patients were characterized as having Stable Angina. Members of the Stable Angina group had undergone coronary angiography (catheterization) documenting the presence of coronary atherosclerosis. No ECG changes were detected, nor were increases in creatine kinase, MB levels or Troponin levels detected.

No plaques—24 Patients with normal coronary arteries. Members of the "No Plaques" group showed no evidence of coronary atherosclerosis following catheritization.

An anti-glycan antibody profile was obtained using GlycoChip™ arrays (Glycominds, Ltd., Lod, Israel, Cat No. 9100) constructed using procedures described in WO00/49412. All sera samples were tested using GlycoChip™ plates (Glycominds Ltd., Lod, Israel, Cat No. 9100), which contained an array of covalently attached mono and oligosaccharide in a reduced volume 384 well micro titer plate. The list of the mono and oligosaccharide displayed on the array as well as their serial numbers are described in Table 4.

Sera were diluted (1:20) in TBST dispensed into a GlycoChip™ plate using a Tecan Genesis Workstation 200 robot (10 μL/well) and incubated 30 min at 25 degrees Celsius. Each glycan and serum sample on the plate was tested 8 times.

The plates were washed with 250 μL/well of high salt buffer (0.15M KNa pH 7.2, NaCl 2M, MgSO4 0.085M, 0.05% Tween20) in an automatic plate washer (Tecan, PowerWasher™). Ten μl/well of biotinylated goat anti-human IgA (Jackson, Pa., USA), 1 μg/ml in TBST, was dispensed manually and the plates incubated for 30 min at 25° C. The plate was washed again with high salt buffer.

Streptavidin-conjugated Europium, Wallac, AD0062 (1 μg/ml, 10 μl/well) was added manually followed by incubation for 30 min at 25° C. in the dark. Washing of the plates with the high salt buffer was repeated. Delfia™ enhancement buffer, (Wallac, 730232, 10 μl/well) was added to the wells and the plates were incubated at least 30 min in the dark. The fluorescence of the wells was read with Victor 1420 (Wallac) using time resolved fluorescence settings Emi. 612 nm and Ext. 340 nm.

The cut off was calculated from the 80th percentile of the normal population According to this definition a number of glycans were identified which had some degree of separating power between the patient groups (see below). "Separation" based on a certain glycan was defined as at least 50% (12/24) positive samples in the "Unstable angina" or "Stable angina" groups, and 5 or less positive samples in the "No plaque" group.

| Glycan LinearCode | | Unstable Angina | Stable Angina | No plaques |
|---|---|---|---|---|
| Ga4Ga | Positives | 12 | 2 | 5 |
| | % Positives | 52 | 8 | 21 |
| Gb | Positives | 19 | 10 | 5 |
| | % Positives | 83 | 42 | 21 |
| ANa | Positives | 13 | 8 | 5 |
| | % Positives | 57 | 33 | 21 |
| ANb | Positives | 15 | 8 | 5 |
| | % Positives | 65 | 33 | 21 |
| GNb4GNb | Positives | 13 | 8 | 5 |
| | % Positives | 57 | 33 | 21 |
| Xa | Positives | 21 | 7 | 5 |
| | % Positives | 100 | 29 | 21 |

These results demonstrate that a combination of glycans Glc (α 1-4) Glc (α), Glc (β), GalNAc (α), GalNAc (β), GlcNAc (β 1-4) GlcNAc (β) and Xylose (α) can be used to successfully distinguish between stable and unstable angina populations. This results demonstrate that it is possible to develop a biomarker based on glycan binding IgA antibodies that distinguishes between Unstable and Stable Angina patients.

EXAMPLE 6

Binding of CD4+ Cells to a Plurality of Glycans Immobilized on a Solid Substrate Binding was examined of CD4+ cells from 7 healthy individuals to 47 different glycans fragments immobilized on a microarray.

Materials and Methods 20 ml of fresh blood from each of the 7 individuals was drawn using 10 ml EDTA-Vaccutainers. Peripheral cell samples were centrifuged (230×g, 900 RPM, 10 minutes at room temperature). The plasma was then separated and the top 2 ml of the cellular fraction transferred to a 15 ml tube. For enrichment of the CD4+ cells, 100 μl RosetteSep reagent was added to the tubes and incubated at room temperature for 20 minutes. The samples were then diluted two-fold in PBS/2% FCS and 5 ml Ficoll is layered under the cell suspension using a glass Pasteur pipette.

Tubes were centrifuged for 30 minutes at room temperature, 2400 RPM (~700×g) with the centrifuge brake off. After centrifugation, tubes were carefully removed from centrifuge. The upper layer was gently drawn off using a sterile pipette, leaving the lymphocyte layer undisturbed at the interface. Using a sterile pipette the leukocyte fraction was transferred to a clean tube, and tube was completely filled with PBS/2% FCS. The cells were washed twice again by centrifugation for 10 minutes, 230×g (1000 RPM) and re-suspended in PBS/2% FCS. Following centrifugations, cells are re-suspended in 500 μl RPMI/1640 2% FCS.

Cells were diluted in Türk solution 1:10 and counted. After counting, cells were diluted to a density of 5×10$^6$ cells/ml in RPMI/1640 2% FCS, then plated in 24 well plate, 1 ml/well. Cell suspensions are incubated over night in 95% humidity, 37° C., 5% $CO_2$ incubator.

To determine cell separation yields by FACS sepearation, 250,000 cells were suspended in 1 ml FACS buffer and then centrifuged 10 minutes at 2000 RPM, 4° C. The supernatant was decanted. The cells were re-suspended in 50 μl FACS buffer and labeled with 5 μl of anti-CD4 antibody. Cells were incubated for 30 minutes on ice, covered from light. 1 ml of ice cold FACS buffer was added and centrifuged 10 minutes, 2000 RPM, 4° C. Cells were then re-suspended in 300 μl FACS buffer, stored on ice and scored on a FACS machine.

GlycoChips were placed in slide holders in plastic vessels embedded with moist paper to retain humidity. Cell suspensions were plated at 1.2 μl/well on the GlycoChip, then incubated in 5% $CO_2$ incubator (95% humidity, 37° C.) for one hour. After incubation, slides were gently placed up-side down in centrifugation chamber immersed in PBS. Glyco-Chips were centrifuged for two minutes at 700 RPM (minimal g force, ~50×g). Slides were observed by microscope and fixed in PBS/3.7% formaldehyde at room temperature for at least 30 minutes. Slides were then washed gently ×3 in DDW and air dried.

Propidium iodide solution was prepared in PBS and plated at 1.2 μl/well. GlycoChips were incubated under humid conditions for 15 minutes then gently rinsed ×3 by dipping in DDW. Slides were air dried in the dark and scanned at propidium iodide settings Ext. 535 nm Emi. 655 nm on an array scanner. The image was analyzed and cell densities were determined.

Results

Figure 20:
FIG. 20 is a histogram showing the binding profile of CD4+ cells from a single individual to various glycans. Glycan structures represented in LINEARCODE® syntax

The glycans and controls used for the binding studies are shown in FIG. 20, below. The structure are written in Linear Code™ syntax, see Table 1 for translation.

Figure 21A:
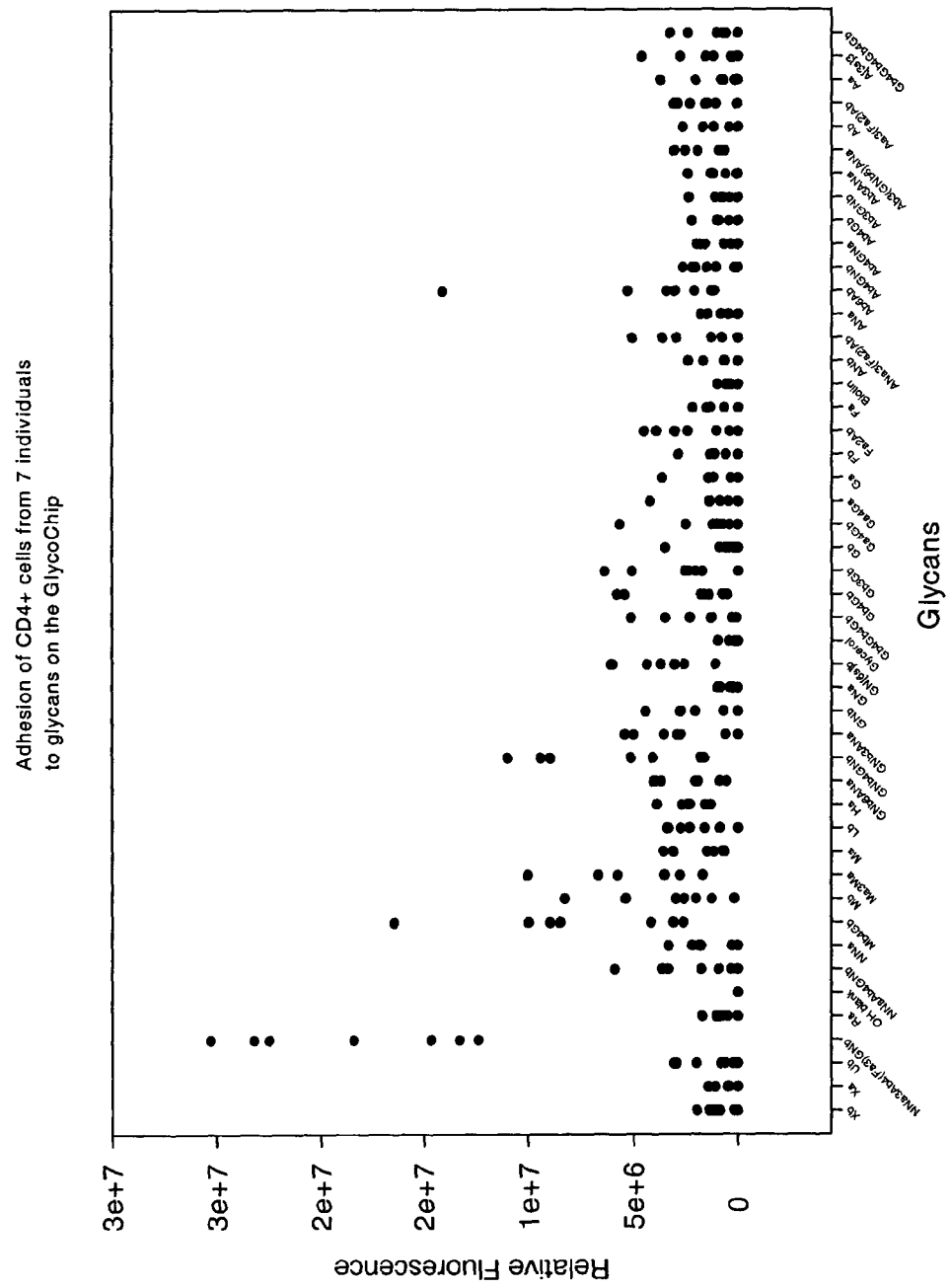
FIG. 21A is a graph showing the median relative fluorescence for CD4+ cells from each of the seven individuals Glycan structures represented in LINEARCODE® syntax.
Figure 21B:
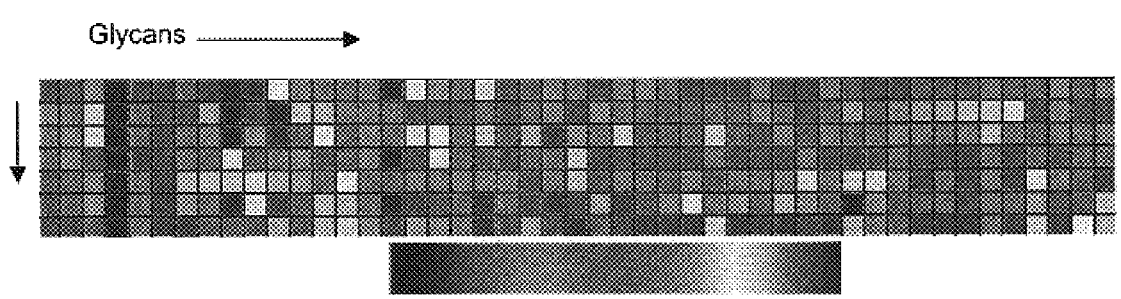
FIG. 21B shows the signals of individual sera against a series of glycans. The anti-glycan antibody binding measured in relative fluorescence units (RFU) were transformed using a histogram equalization-like method which employs a monotonic, non-linear mapping. This way, the RFU values were re-assigned to range between 0 (blue) and 255 (red). The data were clustered using a simulated annealing algorithm.

A histogram showing the binding profile of CD4+ cells from a single individual to various glycans is shown in FIG. 20. Shown is binding in $DLU/mm^2$ for each of the glycans or controls is indicated. CD4+ cell binding to glycans or controls from the seven individuals is shown in FIG. 21A. FIG. 21A shows the median relative fluorescence for CD4+ cells from each of the seven individuals.

These results demonstrate that binding of CD4+ cells varies between the various glycans. The strongest binding was observed to the following glycans, in their order of relative affinity: CD4+ cells bind the following glycans, presented in LinearCode; NNa3Ab4(Fa3)GNb>Mb4Gb>GNb4GNb>Ma3Ma>Ab6Ab. Binding of CD4+ cells to glycans with terminal mannose residues or with Sialyl Lewis X residues was also detected. Variation of CD4+ binding to particular glycans was also detected among the various individuals.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

Tables and Figures:

TABLE 1

Saccharides displayed on the glycan array

| Glycan | IUPAC | LINEARCODE® | Common Name |
|---|---|---|---|
| 0 | pNP-OH | pNP-0 | |
| 1 | Gal (α) | Aa | |
| 2 | Gal (β) | Ab | |
| 3 | Gal (β 1-3) GalNAc (α) | Ab3ANa | |
| 4 | Gal (β 1-3) GlcNAc (β) | Ab3GNb | |
| 5 | Gal (β 1-4) Glc (β) | Ab4Gb | Lactose |
| 6 | Gal (β 1-6) Gal (β) | Ab6Ab | |
| 7 | GalNAc (α) | ANa | |
| 8 | GalNAc (β) | ANb | |
| 9 | Fuc (α) | Fa | |
| 10 | Fuc (β) | Fb | |
| 11 | Glc (α) | Ga | |
| 12 | Glc (α 1-4) Glc (α) | Ga4Ga | Maltose |
| 13 | Glc (α 1-4) Glc (β) | Ga4Gb | |
| 14 | Glc (β) | Gb | |
| 15 | Glc (β 1-4) Glc (β) | Gb4Gb | Cellobiose |
| 16 | Glc (β 1-4) Glc (β 1-4) Glc (β) | Gb4Gb4Gb | Cellotriose |
| 17 | Glc (β 1-4) Glc (β 1-4) Glc (β 1-4) Glc | Gb4Gb4GbGb4Gb | Cellopentaose |
| 18 | Glycerol | Glycerol | |
| 19 | GlcNAc (α) | GNa | |
| 20 | GlcNAc (β) | GNb | |
| 21 | GlcNAc (β 1-3) GalNAc (α) | GNb3ANa | |
| 22 | GlcNAc (β 1-4) GlcNAc (β) | GNb4GNb | Chitobiose |
| 23 | L-Rha (α) | Ha | |
| 24 | GalA (β) | Lb | |
| 25 | Man (α) | Ma | |
| 26 | Man (β) | Mb | |
| 27 | Neu5Ac (α) | NNa | |
| 28 | L-Araf (α) | Ra | |
| 29 | GlcA (β) | Ub | |
| 30 | X(α) | Xa | |
| 31 | X(β) | Xb | |
| 32 | Gal (β1-3) [GlcNAc (β1-6)] GalNAc (α) | Ab3(GNb6)ANa | |
| 33 | Gal (β 1-4) GlcNAc (α) | Ab4GNa | |
| 34 | Gal (α1-3) Gal (β 1-4) GlcNAc (β) | Aa3Ab4GNb | Linear B-2 |
| 35 | Gal (β1-3) Gal (β1-4)GalNAc (β) | Ab4GNb | N-Acetyl |
| 36 | Man (β1-4) GlcNAc (β) | Mb4Gb | |
| 37 | GlcNAc (β1-6)GalNAc (α) | GNb6ANa | |
| 38 | Fuc (α 1-2) Gal (β) | Fa2Ab | |
| 39 | Neu5Ac (α2-3) Gal (β 1-4) [ Fuc (α 1- | NNa3Ab4(Fa3)GNb | Sialyl Lewis X |
| 40 | Man (α 1-3) Man (α) | Ma3Ma | |

TABLE 1-continued

Saccharides displayed on the glycan array

| Glycan | IUPAC | LINEARCODE ® | Common Name |
|---|---|---|---|
| 41 | GlcNAc (β) 6-sulfate | GN[6S]b | |
| 42 | Glc (β 1-3) Glc (β) | Gb3Gb | |
| 43 | Gal(β) 3-sulfate | A[3S]b | |
| 44 | Neu5Ac (α1-3) Gal (β 1-4) GlcNAc (β) | NNa3Ab4GNb | Sialyl lactosamine |
| 45 | Man (α 1-3) [Man (α1-6)] Man (β) | Ma3(Ma6)Mb | |
| 46 | Neu5Ac (α1-3) Gal (β 1-4) Glc (β) | NNa3Ab4Gb | Sialyl lactose |
| 47 | GlcNAc (β 1-3) Gal (α1-4) Glc (β) | GNb3Ab4Gb | Lacto-3 |
| 48 | Gal (α1-4) Gal (β 1-4) Glc (β) | Aa4Ab4Gb | Pk antigen |
| 49 | Neu5Ac (α1-6) Gal (β 1-4) GlcNAc (β) | NNa6Ab4GNb | |
| 50 | Gal (a 1-4) [Fucp (a 1-3)] GlcNAc (b) | Ab4(Fa3)GNb | Lewis X |
| 51 | Neu5Ac (α1-3) Gal (β 1-4) [Fuc (α1-3] | NNa3Ab3(Fa4)GNb | Sialyl Lewis A |
| 52 | Man (α 1-6) Man α | Ma6Ma | |
| 53 | Neu5Ac (α1-3) Gal (β 1-3) GlcNAc (β) | NNa3Ab3GNb | Sialyl Lewis c |
| 54 | Neu5Ac (α1-3) Gal (β 1-3) GalNAc (α) | NNa3Ab3ANa | SiT antigen |

TABLE 2

Number of positive samples having binding signals above the 97% percentile of healthy population.

| Glycan | Result | MS | Healthy |
|---|---|---|---|
| Glc (α) | Positive | 19/42 (45%) | 2/44 (4.5%) |
| | Negative | 23/42 (55%) | 42/44 (96%) |
| Glc (α 1-4) Glc (α) | Positive | 20/42 (48%) | 2/44 (4.5%) |
| | Negative | 22/42 (52%) | 42/44 (96%) |
| Glc (α 1-4) Glc (α) OR Glc (α) | Positive | 25/42 (60%) | 3/44 (6.8%) |
| | Negative | 17/42 (40%) | 41/44 (93%) |

TABLE 3

Number of positive samples having binding signals above the 80% percentile of "stable" MS population.

| Glycan | Result | Attack | Stable | Healthy |
|---|---|---|---|---|
| Glc (α) | Positive | 15/18 (83%) | 5/24 (21%) | 2/44 (4.5%) |
| | Negative | 3/18 (17%) | 19/24 (79%) | 42/44 (96%) |
| Glc (α 1-4) Glc (α) | Positive | 13/18 (72%) | 5/24 (21%) | 2/44 (4.5%) |
| | Negative | 5/18 (28%) | 19/24 (79%) | 42/44 (96%) |
| Glc (α 1-4) Glc (α) OR Glc (α) | Positive | 16/18 (89%) | 7/24 (29%) | 2/44 (4.5%) |
| | Negative | 2/18 (11%) | 17/24 (71%) | 42/44 (96%) |

TABLE 4

| No. | LinearCode ™ |
|---|---|
| 1 | A[3S]b |
| 2 | Aa |
| 3 | Aa3Ab4GNb |
| 4 | Aa4Ab4Gb |
| 5 | Ab |
| 6 | Ab3(GNb6)ANa |
| 7 | Ab3ANa |
| 8 | Ab3GNb |
| 9 | Ab4(Fa3)GNb |
| 10 | Ab4Gb |
| 11 | Ab4GNb |
| 12 | Ab6Ab |
| 13 | ANa |
| 14 | ANb |
| 15 | Fa |
| 16 | Fa2Ab |
| 17 | Fb |
| 18 | Ga |
| 19 | Ga4Ga |
| 20 | Ga4Ga |
| 21 | Gb |
| 22 | Gb3Gb |
| 23 | Gb4Gb4Gb |
| 24 | GN[6S]b |
| 25 | GNa |
| 26 | GNb |
| 27 | GNb3Ab4Gb |
| 28 | GNb3ANa |
| 29 | GNb4GNb |
| 30 | GNb6ANa |
| 31 | Ha |
| 32 | Lb |
| 33 | Ma |
| 34 | Ma3(Ma6)Mb |
| 35 | Ma3Ma |
| 36 | Ma6Ma |
| 37 | Mb |
| 38 | Mb4Gb |
| 39 | NNa3Ab3(Fa4)GNb |
| 40 | NNa3Ab3ANa |
| 41 | NNa3Ab3GNb |
| 42 | NNa3Ab4Gb |
| 43 | NNa3Ab4GNb |
| 44 | NNa6Ab4GNb |
| 45 | OH |
| 46 | Ra |
| 47 | NNa3Ab4(Fa3)GNb |
| 48 | Ub |
| 49 | Xa |
| 50 | Xb |

TABLE 5

Table 5. Saccharides displayed on glycan array and level of anti-glycan

| Glycan No. | Glycan | Linear Code ®[11] | Ab Binding (RFU)[a] | Relative Ab |
|---|---|---|---|---|
| 0 | pAP | — | NA | NA |
| 1 | Gal (α) | Aa | 181,069 | 10 |
| 2 | Gal (β) | Ab | 119,034 | 14 |
| 3 | Gal (β 1-3) GalNAc (α) | Ab3Ana | 52,853 | |
| 4 | Gal (β 1-3) GlcNAc (β) | Ab3GNb | 58,239 | |
| 5 | Gal (β 1-4) Glc (β) | Ab4Gb | 92,170 | |
| 6 | Gal (β 1-6) Gal (β) | Ab6Ab | 151,313 | 11 |
| 7 | GalNAc (α) | ANa | 64,429 | |
| 8 | GalNAc (β) | ANb | 57,832 | |
| 10 | Fuc (α) | Fa | 47,727 | |
| 11 | Fuc (β) | Fb | 63,782 | |
| 12 | Glc (α) | Ga | 109,091 | |
| 13 | Glc (α 1-4) Glc (α) | Ga4Ga | 80,024 | |
| 14 | Glc (α 1-4) Glc (β) | Ga4Gb | 127,594 | 13 |
| 15 | Glc (β) | Gb | 112,513 | |
| 16 | Glc (β 1-4) Glc (β) | Gb4Gb | 239,830 | 9 |
| 17 | Glc (β 1-4) Glc (β 1-4) | Gb4Gb4 | 284,361 | 7 |
| 18 | Glc (β 1-4) Glc (β 1-4) | Gb4Gb4 | 311,235 | 5 |
| 19 | Glycerol | Glycerol | 52,884 | |
| 20 | GlcNAc (α) | GNa | 1,031,130 | 1 |
| 21 | GlcNAc (β) | GNb | 311,341 | 4 |
| 22 | GlcNAc (β 1-3) GalNAc | GNb3A | 294,624 | 6 |
| 23 | GlcNAc (β 1-4) GlcNAc | GNb4G | 433,604 | 3 |
| 24 | L-Rha (α) | Ha | 662,337 | 2 |
| 25 | GalA (β) | Lb | 96,801 | |
| 26 | Man (α) | Ma | 83,647 | |
| 27 | Man (β) | Mb | 77,533 | |
| 28 | Neu5Ac (α) | NNa | 52,028 | |
| 29 | L-Araf (α) | Ra | 51,230 | |
| 30 | GlcA (β) | Ub | 56,719 | |
| 31 | X(α) | Xa | 55,806 | |
| 32 | X(α) | Xb | 78,776 | |
| 33 | Gal (β1-3) [GlcNAc | Ab3(GN | 84,080 | |
| 34 | Gal (β 1-4) GlcNAc (α) | Ab4GNa | 143,036 | 12 |
| 36 | Gal (β1-3) Gal (β1- | Aa3Ab4 | 268,549 | 8 |

What is claimed is:

1. A method of diagnosing multiple sclerosis in a subject, the method comprising
providing a blood sample from a subject; detecting in said blood sample an anti-Glc (α1-4) Glc (α)IgM type antibody; and
comparing the levels of said antibody in said blood sample to the levels of said antibody in a normal control sample, wherein a higher level of said antibody in said blood sample compared to the level of said antibody in a normal control sample is indicative of multiple sclerosis,
thereby diagnosing multiple sclerosis in said subject, wherein said diagnosis is after a first neurological attack and prior to a second neurological attack.

2. The method of claim 1, wherein said method further comprises
detecting a second antibody, wherein said second antibody is an anti-Glc $(\alpha)_{13}$IgM type antibody, and
comparing the levels of the second antibody in said blood sample to the levels of the second antibody in a normal control sample, wherein a higher level of said antibody in said blood sample compared to the level of said antibody in a normal control sample is indicative of multiple sclerosis;
thereby diagnosing multiple sclerosis in said subject.

3. The method of claim 1, wherein said control sample is obtained from a population of one or more individuals that do not show multiple sclerosis symptoms.

4. The method of claim 1, wherein said subject is a female.

5. The method of claim 1, wherein said subject is a male.

6. The method of claim 1, wherein said normal control sample is obtained from a group consisting of one or more individuals, wherein said group consisting of one or more individuals is determined using an Expanded Disability Status Scale (EDSS) assessment or a Magnetic Resonance Imaging (MRI) assessment.

7. The method of claim 1, wherein said normal control sample is obtained from a group consisting of one or more individuals, wherein said group consisting of one or more individuals is determined using an Expanded Disability Status Scale (EDSS) assessment.

* * * * *

UNITED STATES PATENT AND TRADEMARK OFFICE
CERTIFICATE OF CORRECTION

PATENT NO.        : 7,537,900 B2
APPLICATION NO.   : 10/634309
DATED             : May 26, 2009
INVENTOR(S)       : Dotan et al.

It is certified that error appears in the above-identified patent and that said Letters Patent is hereby corrected as shown below:

Column 23, line 55, claim 2, "is an anti-Glc $(\alpha)_{13}$IgM type antibody, and" should read --is an anti-Glc $(\alpha)$ IgM type antibody, and--.

Signed and Sealed this

Fourteenth Day of July, 2009

JOHN DOLL
*Acting Director of the United States Patent and Trademark Office*

UNITED STATES PATENT AND TRADEMARK OFFICE
CERTIFICATE OF CORRECTION

PATENT NO. : 7,537,900 B2
APPLICATION NO. : 10/634309
DATED : May 26, 2009
INVENTOR(S) : Dotan et al.

Page 1 of 1

It is certified that error appears in the above-identified patent and that said Letters Patent is hereby corrected as shown below:

On the cover page,

Item [*] Notice: Subject to any disclaimer, the term of this patent is extended or adjusted under 35 USC 154(b) by (436) days Delete the phrase "by 436 days" and insert --by 447 days--

Signed and Sealed this

Twenty-seventh Day of October, 2009

David J. Kappos
*Director of the United States Patent and Trademark Office*